(12) United States Patent
Wedding et al.

(10) Patent No.: US 9,694,094 B1
(45) Date of Patent: *Jul. 4, 2017

(54) ULTRAVIOLET PLASMA-SHELLS

(71) Applicants: Tricia N. Wedding, Toledo, OH (US); Carol Ann Wedding, Toledo, OH (US)

(72) Inventors: Tricia N. Wedding, Toledo, OH (US); Carol Ann Wedding, Toledo, OH (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/922,463

(22) Filed: Oct. 26, 2015

Related U.S. Application Data

(63) Continuation-in-part of application No. 14/341,233, filed on Jul. 25, 2014, now Pat. No. 9,168,320, which is a continuation-in-part of application No. 13/448,355, filed on Apr. 16, 2012, now abandoned, which is a continuation-in-part of application No. 12/987,209, filed on Jan. 10, 2011, now abandoned.

(60) Provisional application No. 61/293,232, filed on Jan. 8, 2010.

(51) Int. Cl.
| | |
|---|---|
| *A61L 2/08* | (2006.01) |
| *B01J 19/08* | (2006.01) |
| *A61L 9/20* | (2006.01) |
| *A61L 2/10* | (2006.01) |

(52) U.S. Cl.
CPC .............. *A61L 2/088* (2013.01); *A61L 2/10* (2013.01); *A61L 9/205* (2013.01); *B01J 19/088* (2013.01); *B01J 2219/0847* (2013.01)

(58) Field of Classification Search
None
See application file for complete search history.

(56) References Cited

U.S. PATENT DOCUMENTS

| | | |
|---|---|---|
| 2,636,991 A | 4/1953 | Postell |
| 3,418,069 A | 12/1968 | Decupper |
| 3,576,593 A | 4/1971 | Cicirello |
| 3,634,025 A | 1/1972 | Landry |
| 3,906,236 A | 9/1975 | Callahan |
| 4,033,719 A | 7/1977 | Conn et al. |
| 4,563,589 A | 1/1986 | Scheffer |
| 4,772,795 A | 9/1988 | Sakurai et al. |
| 4,798,702 A | 1/1989 | Tucker |
| 4,969,991 A | 11/1990 | Valadez |
| 4,983,411 A | 1/1991 | Tanaka et al. |
| 5,166,528 A | 11/1992 | Le Vay |
| D350,181 S | 8/1994 | MacNeal |
| D358,637 S | 5/1995 | Boehme |
| 5,445,729 A | 8/1995 | Monroe et al. |
| 5,785,845 A | 7/1998 | Colaiano |
| 6,087,774 A | 7/2000 | Makayama et al. |
| 6,207,118 B1 | 3/2001 | Gaven et al. |
| 6,570,173 B1 | 5/2003 | Kunkel et al. |
| 6,627,268 B1 | 9/2003 | Fair et al. |
| 6,656,424 B1 | 12/2003 | Deal |
| D485,364 S | 1/2004 | Lee |
| 6,685,826 B1 | 2/2004 | James |
| 6,709,574 B2 | 3/2004 | James |
| 6,916,452 B1 | 7/2005 | Rix et al. |
| 7,160,441 B2 | 1/2007 | Gannon et al. |

(Continued)

*Primary Examiner* — Kishor Mayekar
(74) *Attorney, Agent, or Firm* — Donald K. Wedding

(57) ABSTRACT

Method and apparatus for generating UV and for treating a material with UV utilizing gas filled plasma-shells that emit UV during gas discharge. The UV treatment includes UV curing or inducing a chemical reaction.

18 Claims, 21 Drawing Sheets

(56) References Cited

U.S. PATENT DOCUMENTS

| | | |
|---|---|---|
| 7,380,627 B2 | 6/2008 | Huang et al. |
| 7,431,848 B2 | 10/2008 | James |
| 7,897,215 B1 | 3/2011 | Fair et al. |
| 8,138,673 B1 * | 3/2012 | Wedding .................. H01J 11/18 |
| | | 313/567 |
| 8,458,923 B2 | 6/2013 | Mackinnon et al. |
| 9,168,320 B1 * | 10/2015 | Wedding ................... A61L 2/10 |
| 2004/0247779 A1 | 12/2004 | Selvamanickam et al. |
| 2006/0233501 A1 | 10/2006 | Sampson |
| 2007/0249128 A1 | 10/2007 | Kim et al. |
| 2008/0135399 A1 | 6/2008 | Mukaddam et al. |
| 2015/0132973 A1 | 5/2015 | Hung et al. |

* cited by examiner

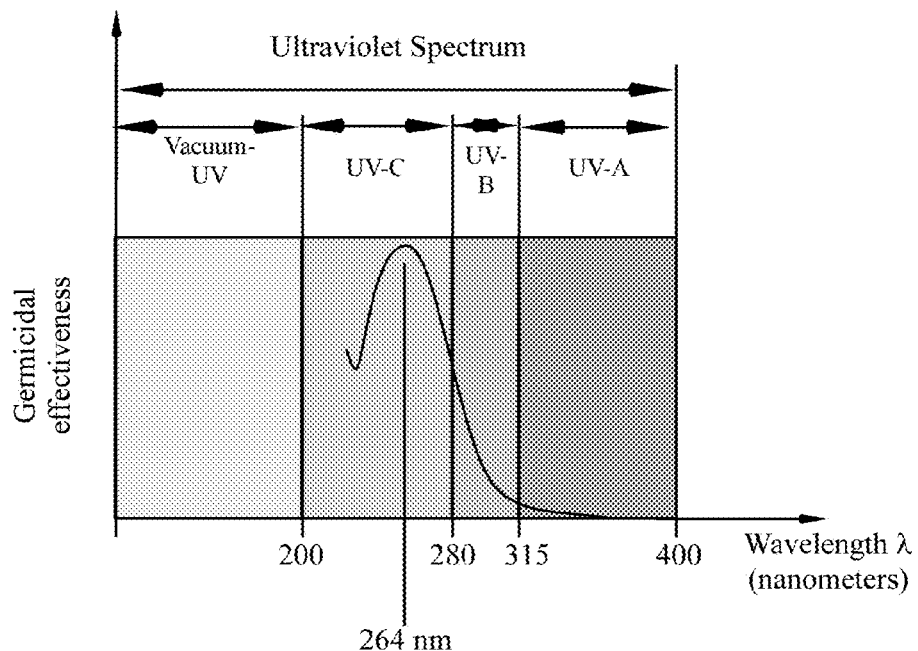
*FIG. 3B*
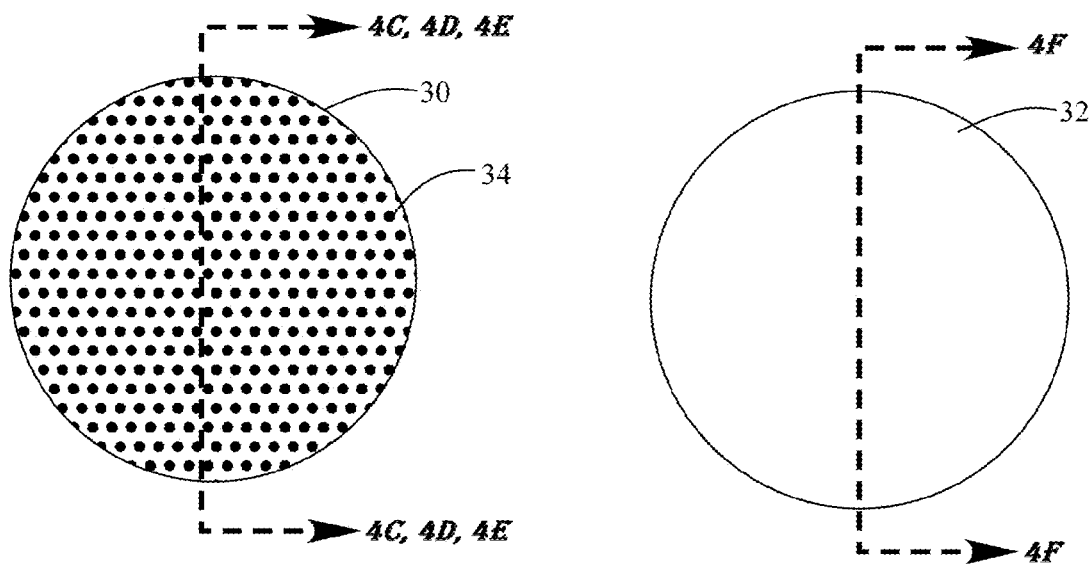
*FIG. 4A*                    *FIG. 4B*

FIG. 5                    FIG. 5A

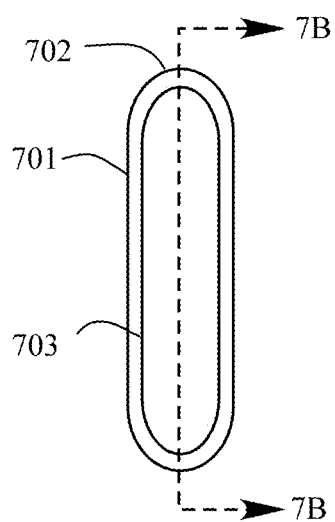
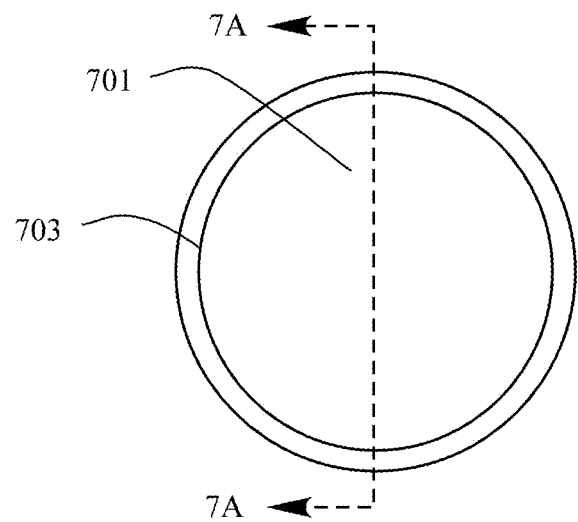
FIG. 7A
FIG. 7B

ULTRAVIOLET PLASMA-SHELLS

RELATED APPLICATIONS

This application is a continuation-in-part under 35 U.S.C. 120 of copending U.S. patent application Ser. No. 14/341,233 filed Jul. 25, 2014 to issue as U.S. Pat. No. 9,168,320 which is a continuation-in-part under 35 U.S.C. 120 of copending U.S. patent application Ser. No. 13/448,355 filed Apr. 16, 2012 which is a continuation-in-part under 35 U.S.C. 120 of copending U.S. patent application Ser. No. 12/987,209 filed Jan. 10, 2011 which claims priority under 35 U.S.C. 119(e) for U.S. Provisional Application Ser. No. 61/293,232 Filed Jan. 8, 2010, all incorporated herein by reference.

FIELD OF THE INVENTION

This invention relates to an ultraviolet (UV) sterilization method utilizing plasma-shells to purify a material or substance including liquids, gases, and/or solids particularly the surface of a solid.

Ultraviolet plasma-shells may be used in Photo-Initiated Chemical Vapor Deposition processes (PICVD). This process uses UV light to stimulate chemical reactions. It is similar to plasma processing. Under certain conditions, PICVD can be operated at or near atmospheric pressure.

Ultraviolet plasma-shells may also be used in Ultraviolet curing devices. Ultraviolet curing (UV curing) is a photochemical process in which high-intensity ultraviolet light is used to instantly cure or "dry" inks, coatings or adhesives. UV curing has been shown to increase production speed, reduce reject rates, improve scratch and solvent resistance, and facilitate superior bonding.

The plasma-shells are encapsulated, hollow, gas-filled shells. When energy is applied across the plasma-shell, the gas ionizes and glows. Depending on the type of ionized gas, the gas discharge will emit photons or light in the UV, visible, and/or infrared regions. The ionized gas can be used alone or in combination with a luminescent material to achieve light emission in the UV, visible, and/or infrared region. The plasma-shell may be of any suitable geometric shape, such as a plasma-sphere, plasma-disc, plasma-dome, plasma-cube, plasma-cuboid, and/or an elongated plasma-tube. Plasma-shells are closely packed in an array to provide a homogenous lambertian light source devoid of hot spots and shadows.

BACKGROUND OF THE INVENTION

Ultraviolet radiation has been known as a cellular mutagen for over 100 years. UV sterilizers utilize UV light wavelengths in the range of about 210 nm (nanometers) to about 290 nm. Gases that emit light in the UV wavelength range of about 10 nm to 400 nm are mercury vapor, hydrogen, nitrogen, oxygen, fluorine, bromine, iodine, helium, neon, argon, krypton, xenon, radon, mixtures of gases also produce light in the near UV range. Some gases include, but are not limited to, xenon mixed with halides and hydrogen mixed with ammonia. Since mercury vapor emits UV at a wavelength of 254 nm, which is near the center of the germicidal range, mercury vapor is widely used as the excitable gas in UV sterilizers.

There are many UV sterilizers on the market today. There are many advantages for using plasma-shells over traditional tube-type lamps. The plasma-shells are more rugged than traditional quartz lamps. The plasma-shells have a greater overall surface area, thereby increasing the amount of UV light that can be used to sterilize liquids, gases, and/or solids. UV light is used in medical applications. UV light is used in to photo cure materials such as polymers and dental ceramics. The shell material of a plasma-shell may be selected to provide increased UV emission. The plasma-shell produces less heat than traditional quartz lamps with a lifespan. Quartz lamps typically use dangerous mercury vapor to generate UV emission. These lamps need to be managed according to special disposal laws and regulations. Rare gases used alone or in combination with rare gases and/or other gases discussed herein such as neon, argon, xenon, krypton, and helium may be used in plasma-shells and do not require any special disposal procedures.

THE INVENTION

In accordance with this invention, there is provided UV sterilization using plasma-shells to purify a selected substance or material.

In one embodiment of this invention, a multiplicity of gas-filled shells are used to emit photons or light in the UV region to sterilize a solid including the surface such as food or surgical instruments. When the UV sterilizer is included in the packaging system in the food packaging industry, it uses a lethal dose of UV radiation to break down the DNA of any microbiological organism that passes through it, effectively killing the microorganism, or rendering it incapable of reproducing or causing infection, without harming or otherwise impacting the merchandise.

In another embodiment, a multiplicity of gas-filled shells are used to emit photons in the UV region to sterilize a liquid including, but not limited to, water. When the UV sterilizer is included in the plumbing supply system of a pond, aquarium, home, swimming pool, hot-tub, spa, laboratory, sewage treatment plant, etc., it uses a lethal dose of UV radiation to break down the DNA of any microbiological organism that passes through it, effectively killing the microorganism, or rendering it incapable of reproducing or causing infection.

In another embodiment, a multiplicity of gas-filled shells are used to emit photons in the UV region to sterilize a gas including, but not limited to, air. When the UV sterilizer is included in the HVAC supply system of a home, business, laboratory, etc., it uses a lethal dose of UV radiation to break down the DNA of any microbiological organism that passes through it, effectively killing the microorganism, or rendering it incapable of reproducing or causing infection. The gas in the plasma-shell is discharged by an energy transmission causing UV photon or light emission from the plasma-shell. The gas-filled shells may be isolated or interconnected by one or more electrodes connected to electronic circuitry. The plasma-shell may be of any suitable geometric shape, including a plasma-sphere, plasma-disc, plasma-dome, plasma-cube, plasma-cuboid, and/or an elongated plasma-tube. Other geometric shapes are illustrated herein.

A plasma-sphere is a primarily hollow sphere with relatively uniform shell thickness. The shell is typically composed of a dielectric material. It is filled with an ionizable gas at a desired mixture and pressure. The gas discharges when a voltage is applied and produces visible, UV, and/or infrared photons or light. The shell material is selected to optimize dielectric properties and optical transmissivity. Additional beneficial materials may be added to the inside or outer surface of the sphere including magnesium oxide for secondary electron emission. The magnesium oxide and other materials including organic and/or inorganic luminescent substances may be added directly to the shell material.

A plasma-disc is similar to the plasma-sphere in material composition and ionizable gas selection. It differs from the plasma-sphere in that it is flattened on both the top and bottom. A plasma-sphere or sphere may be flattened to form a plasma-disc by applying heat and pressure simultaneously to the top and bottom of the sphere using two substantially flat and ridged members, either of which may be heated. The plasma-disc may have sides or edges, which are round, curved, flat, or angled. The top and bottom are substantially flat and may have one or more flattened sides. The top and bottom can be substantially the same area or be different areas. The top and bottom can be substantially parallel to one another or not parallel to one another.

A plasma-dome is similar to a plasma-sphere in material composition and ionizable gas selection. It differs in that one side is domed. A plasma-sphere is flattened on one or more other sides to form a plasma-dome, typically by applying heat and pressure simultaneously to the top and bottom of the plasma-sphere or sphere using one substantially flat and ridged member and one substantially elastic member. In one embodiment, the substantially rigid member is heated.

A plasma-cube is a hollow cube with six flat sides. It is a regular shape with six congruent square faces, the angle between any two adjacent faces being a right angle. It can be formed on a mold under pressure with or without heat.

A plasma-cuboid is a hollow cube with six flat sides of different dimensions. The cross-section along any axis is a rectangle, trapezoid, parallelogram, or other flat, four sided shape. It is also known as a rectangular parallelepiped. It can be made in the same way as a cube.

A plasma-tube is an elongated hollow body of any suitable geometric shape and cross-section. Contemplated cross-sectional shapes include circle, ellipse, oval, triangle, square, rectangle, pentagon, hexagon, and so forth. It differs from the plasma-sphere in that it is elongated and flattened on both the top and bottom. The plasma-tube may have sides or edges, which are round, curved, flat, or angled. The top and bottom are substantially flat and may have one or more flattened sides. The top and bottom can be substantially the same area or be different areas. The top and bottom can be substantially parallel to one another or not parallel to one another.

A plasma-prism is similar to plasma-sphere in material composition and ionizable gas selection. It is a hollow polyhedron with two congruent and parallel bases, whose lateral faces are parallelograms. The bases may consist of three or more sides, for example triangular prisms, pentagonal prisms, and hexagonal prisms. The bases of the triangular prisms may be equilateral, scalene, acute, obtuse, right, or isosceles triangles.

A plasma-pyramid is similar to plasma-sphere in material composition and ionizable gas selection. It is a hollow polyhedron with a polygonal base and triangular sides that meet at a common vertex. The polygonal bases may consist of three or more sides, for example triangular pyramids, square pyramids, pentagonal pyramids, and hexagonal pyramids.

A plasma-cone is similar to plasma-sphere in material composition and ionizable gas selection. It is a hollow object that tapers from a roughly circular base to a vertex. The base may be, but not limited to, circular or elliptical.

BRIEF DESCRIPTION OF THE DRAWINGS

FIG. 3B shows the ultraviolet spectrum of light vs. germicidal effectiveness.

FIG. 4A shows a plasma-sphere embodiment from any side.

FIG. 4B shows another plasma-sphere embodiment from any side.

FIGS. 5, 5A, and 5B show a plasma-dome with one flat side.

FIGS. 7A and 7B show a plasma-disc.

FIGS. 9, 9A, and 9B show a plasma-cube.

DETAILED DESCRIPTION OF THE DRAWINGS

Figure 1:
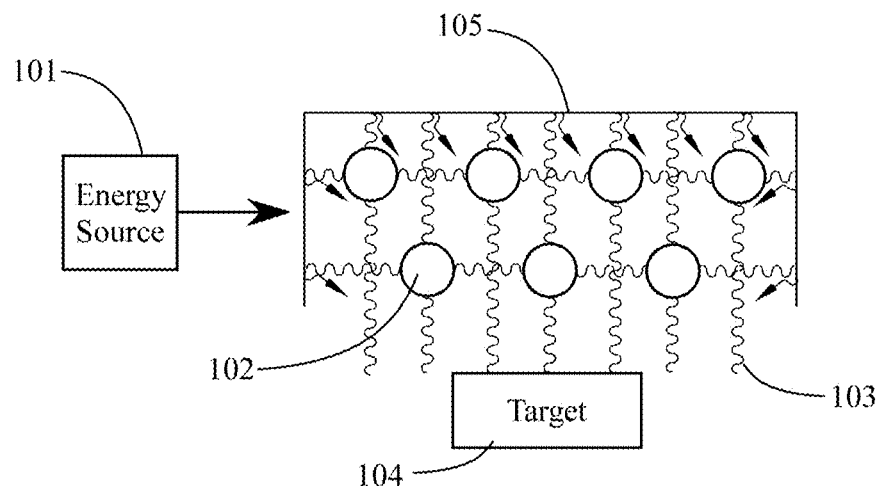
FIG. 1 shows one method for sterilizing the surface of a target.

FIG. 1 illustrates a method of sterilizing or sanitizing the surface of a target 104. An energy source 101 is used to excite the gas inside plasma-shells 102. Ultraviolet (UV) radiation 103 in the germicidal wavelength ($\lambda$) range of 210 nm to 290 nm is emitted from the gas discharge in the plasma-shells 102. Because UV light is emitted in all directions from the plasma-shells 102, a reflector 105 may be used to direct UV light toward the surface of the target 104 for greater efficiency. Although plasma-spheres are illustrated, plasma-shells of different geometric shapes may be used alone or in combination with plasma-spheres. The energy source 101 may be radio frequency (RF) or voltages applied with electrodes.

Figure 2A:
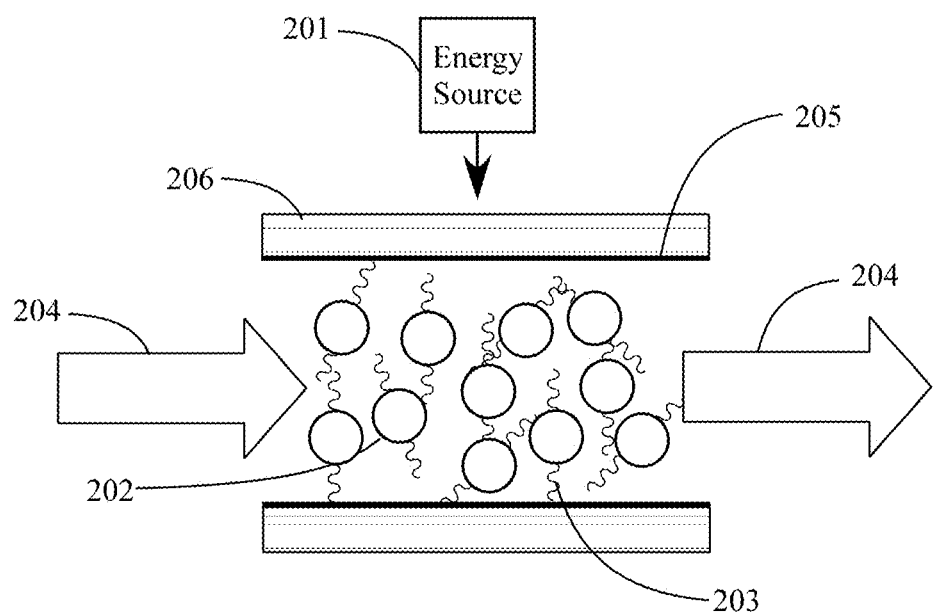
FIGS. 2A, 2B, 2C, and 2D are diagrams of possible methods of sterilizing a liquid such as water.

FIG. 2A illustrates a method for sterilizing a liquid or gas 204 such as water or air flowing through a pipe or tube 206. An energy source 201 is used to excite the gas inside plasma-shells 202. Ultraviolet (UV) radiation 203 in the germicidal wavelength (λ) range of 210 nm to 290 nm is emitted from the plasma-shells 202. Since UV light is emitted in all directions from the plasma-shells 202, a reflector 205 may be used on the inside of the pipe 206 to direct UV light back into the liquid 201 for greater efficiency. The liquid 204 is forced to flow around the plasma-shells 202, which are located in the pipe 206, thereby exposing all of the liquid or fluid 201 to the sterilizing UV light. Although plasma-spheres are illustrated, plasma-shells of different geometric shapes may be used alone or in combination with plasma-spheres. The embodiment of FIG. 2A can also be used inside of an autoclave. In this embodiment, a solid article such as a surgical tool can be placed directly into the bed of plasma-shells. When the plasma-shells are energized, they will flood the solid article with photons of UV light from all directions.

Figure 2B:
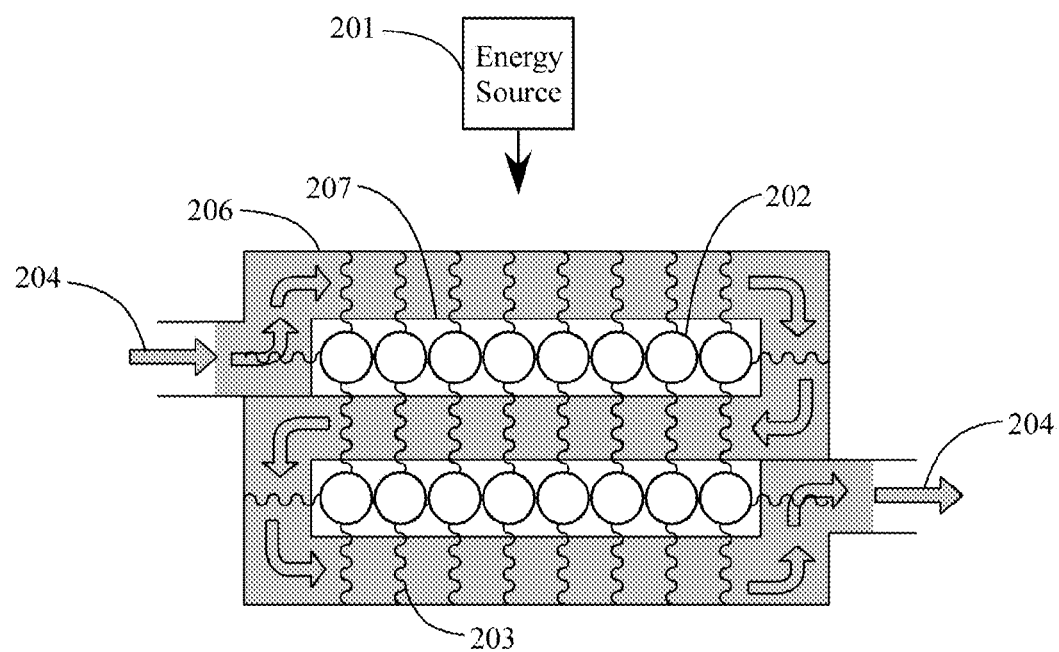

FIG. 2B is a diagram of one possible method of sterilizing a fluid such as a liquid or gas 204 flowing through a pipe or tube 206. An energy source 201 is used to excite the gas inside plasma-shells 202. Ultraviolet (UV) radiation 203 in the germicidal wavelength (λ) range of 210 nm to 290 nm is emitted from the plasma-shells 202. UV light is emitted in all directions from the plasma-shells 202 and a reflector, not shown, may be used to direct UV light back into the fluid 204 for greater efficiency. In this embodiment, water 204 or other fluid is flowed through the pipe or tube 206 that winds its way between two other UV transmissive pipes or tubes 207 containing plasma-shells. Although plasma-spheres are illustrated, plasma-shells of different geometric shapes may be used alone or in combination with plasma-spheres.

Figure 2C:
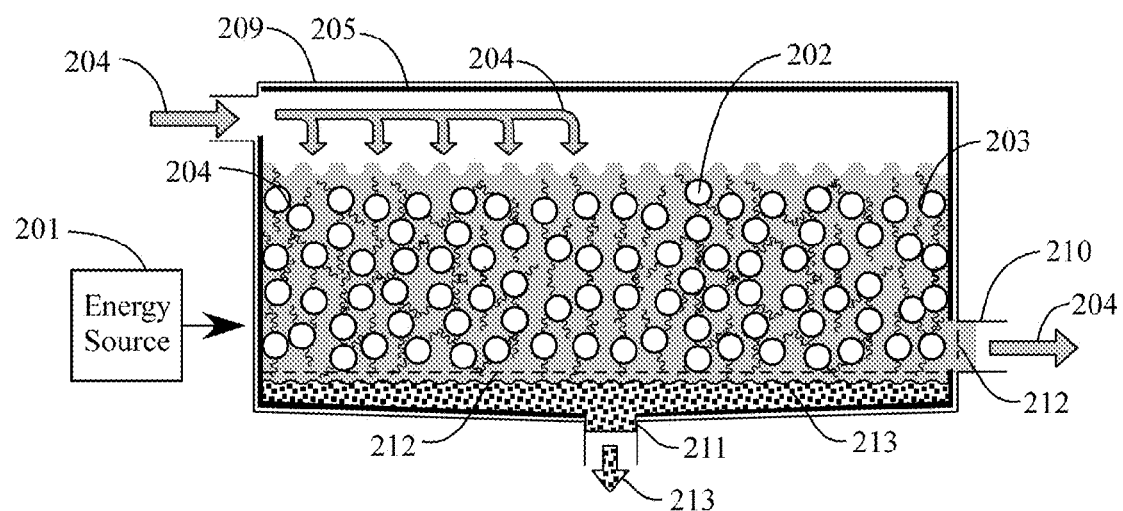

FIG. 2C illustrates a method for sterilizing a fluid 204 such as water or gas flowing into a container 209 containing a bed of plasma-shells 202. An energy source 201 is used to excite the gas inside plasma-shells 202. Ultraviolet (UV) radiation 203 in the germicidal wavelength (λ) range of 210 nm to 290 nm is emitted from the gas discharge in the plasma-shells 202. UV light is emitted in all directions from the plasma-shells 202 and a reflector 205 may be used to direct UV light back into the fluid 204 for greater efficiency. The fluid 204 is flowed through the bed of plasma-shells 202, located in holding container 209, by the force of gravity, thereby exposing all of the fluid 204 to the sterilizing UV light.

The fluid 204, such as water or gas, flows into the holding container 209, such as a cistern. The holding container 209 may be lined with a reflector 205 as shown. The reflector 205 may act not only to excite the plasma-shells 202 with energy from the energy source 201, but also as a reflector to redirect the UV light back into the fluid 204 for greater efficiency. Once the fluid 204 has been sanitized, it drains via a drainage pipe 210. A screen or mesh 212 can be used to prevent the plasma-shells 202 from draining with the fluid 204. The added advantage of this embodiment is that any solid particulate matter or sediment 213 mixed with the fluid 204 may be mechanically filtered from the fluid 204, and settled at the bottom of the container 209. A screen or mesh 212 can be used to prevent the plasma-shells 202 from mixing with the sediment 213. The sediment 213 may be drained from the bottom of the chamber through the solid waste drain 211. Although plasma-spheres are illustrated, plasma-shells of different geometric shapes may be used alone or in combination with plasma-spheres.

Figure 2D:
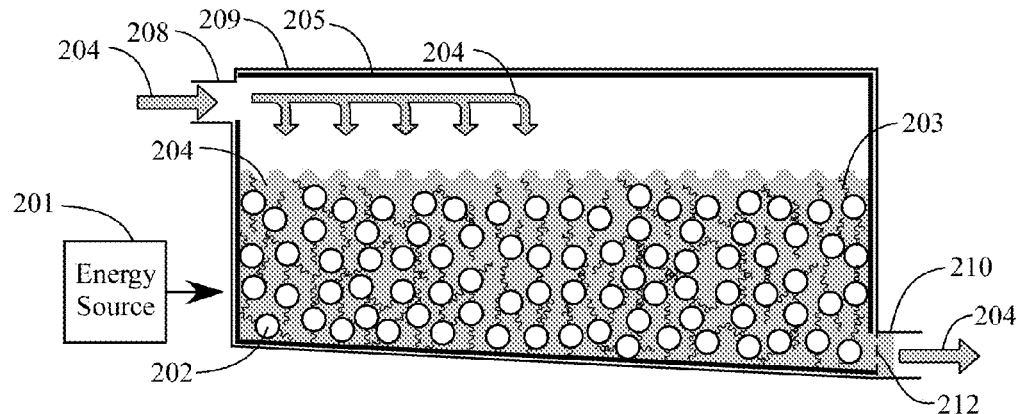

FIG. 2D illustrates a method for sterilizing a fluid 204 such as liquid or gas 204. An energy source 201 is used to excite the gas inside plasma-shells 202. Ultraviolet (UV) radiation 203 in the germicidal wavelength (λ) range of 210 nm to 290 nm is emitted from the plasma-shells 202. UV light is emitted in all directions from the plasma-shells 202 and a reflector 205 may be used to direct UV light back into the fluid 204 for greater efficiency. The fluid 204 is forced to gravity flow through a bed of plasma-shells 202, which are located in holding container 209, thereby exposing all of the fluid 204 to the sterilizing UV light.

The fluid 204, such as water, flows into a holding container 209 illustrated with a sloped bottom, such as a cistern. The holding container 209 may be lined with a reflector 205. The reflector 205 may act not only to excite the plasma-shells with energy from the energy source 201, but also as a reflector to redirect the UV light back into the fluid 204 for greater efficiency. Once the fluid has been sanitized, it drains via a drainage pipe 210. A screen or mesh 212 can be used to prevent the plasma-shells 202 from draining with the fluid 204. Although plasma-spheres are illustrated, plasma-shells of different geometric shapes may be used alone or in combination with plasma-spheres.

Figure 3A:
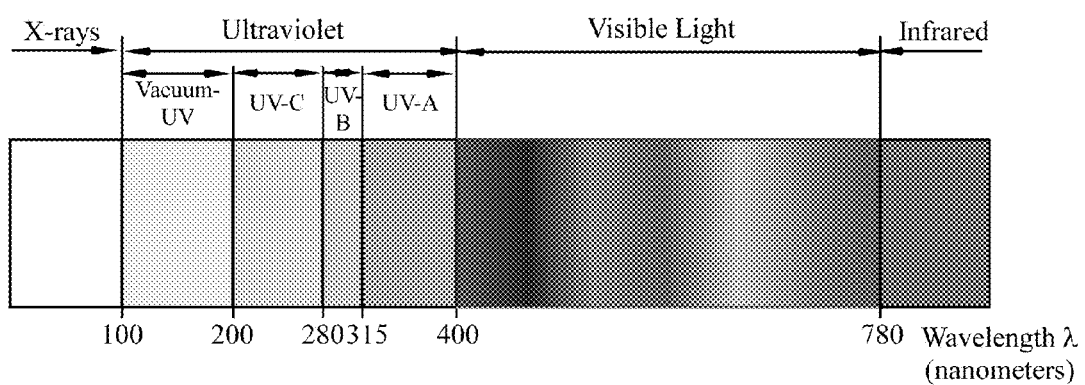
FIG. 3A shows the electromagnetic spectrum of light.

FIG. 3A shows the electromagnetic spectrum of light. Electromagnetic radiation (often abbreviated E-M radiation or EMR) is a ubiquitous phenomenon that takes the form of self-propagating waves in a vacuum or in matter. It consists of electric and magnetic field components which oscillate in phase perpendicular to each other and perpendicular to the direction of energy propagation. Electromagnetic radiation is classified into several types according to the frequency of its wave; these types include (in order of increasing frequency and decreasing wavelength): radio waves, microwaves, terahertz radiation, infrared radiation, visible light, ultraviolet radiation, X-rays and gamma rays. A small and somewhat variable window of frequencies is sensed by the eyes of various organisms; this is what we call the visible spectrum, or light. EM radiation carries energy and momentum that may be imparted to matter with which it interacts.

FIG. 3B shows the ultraviolet spectrum of light vs. germicidal effectiveness. Ultraviolet lamps are used to sterilize workspaces and tools used in biology laboratories and medical facilities. Commercially-available low pressure mercury-vapor lamps emit about 86% of their light at 254 nanometers (nm) which coincides very well with one of the two peaks of the germicidal effectiveness curve (i.e., effectiveness for UV absorption by DNA). One of these peaks is at about 265 nm and the other is at about 185 nm. Although 185 nm is better absorbed by DNA, the quartz glass used in commercially-available lamps, as well as environmental media such as water, are more opaque to 185 nm than 254 nm (C. von Sonntag et al., 1992). UV light at these germicidal wavelengths causes adjacent thymine molecules on DNA to dimerize, if enough of these defects accumulate on a microorganism's DNA its replication is inhibited, thereby rendering it harmless (even though the organism may not be killed outright).

FIG. 4A illustrates a plasma-shell 30 from any viewing angle. The plasma-shell is illustrated in the shape of a sphere, but other geometric shapes may be used. The plasma-shell 30 is comprised in whole or in part of material 34 that is transmissive to UV radiation. Such materials include various transparent oxides including, but not limited to, aluminum oxide such as alumina ($Al_2O_3$).

FIG. 4B illustrates a plasma-shell (not shown) from any viewing angle. The plasma-shell is illustrated in the shape of a sphere, but other geometric shapes may be used. The plasma-shell is coated with a thin film layer of a beneficial material 32. Such materials include, but are not limited to, titanium oxide including titanium dioxide ($TiO_2$) and titanium oxide including $TiO_2$ doped with tungsten trioxide. When titanium dioxide is exposed to UV radiation, it photocatalyzes producing a germicidal effect.

Figure 4C:
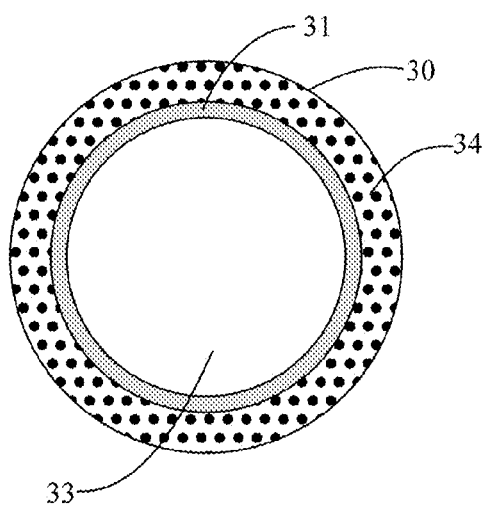
FIG. 4C shows a cross-section view of a plasma-sphere embodiment.

FIG. 4C illustrates a section 4C-4C view of the UV plasma-shell 30. The plasma-shell illustrated is a plasma-sphere. The plasma-shell 30 is comprised in whole or in part of material 34 that is transmissive to UV radiation. Such materials include various transparent oxides including, but not limited to, aluminum oxide including $Al_2O_3$. The plasma-shell 30 is impervious and encapsulates a gas 33 that when energized, emits energy in the vacuum ultraviolet (VUV) region. Such gases include, but are not limited to, xenon and mixtures of xenon. Xenon is known to emit strong VUV at wavelengths of about 142 nm and about 173 nm. The VUV emitting gas excites a luminescent material 31, such as a phosphor, that may partially coat or wholly coats the interior of the plasma-shell 30. Such VUV to UV phosphors include, but are not limited to, $LaPO_4$:Pr, $YPO_4$:Pr, $Sr(Al,Mg)_{12}O_{19}$:Pr, $Ca_2P_2O_7$:Pr,Na, and $CaSO_4$:Pb. Optionally other beneficial materials may be added to at least a portion of the inner surface including materials to encourage ionization of the gas or protection of the phosphor 31. Such optional materials include, but are not limited to, MgO, diamond, carbon nanotubes, $LaB_6$ and lanthanum strontium manganite (LSM). Optional electrodes may be added to the exterior or interior of the plasma-shell 30 to concentrate charge.

Figure 4D:
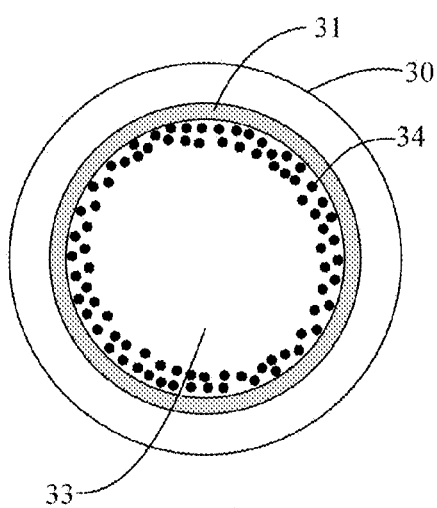
FIG. 4D shows a cross-section view of a plasma-sphere embodiment.

FIG. 4D illustrates a section 4D-4D view of the UV plasma-shell 30. The plasma-shell illustrated is a plasma-sphere. The plasma-shell 30 is lined with a luminescent material 31 and a material 34 that is transmissive to UV radiation. Such UV transmissive materials include various transparent oxides including, but not limited to, aluminum oxide ($Al_2O_3$) also known as alumina. The plasma-shell 30 is impervious and encapsulates a gas 33 that when energized emits energy in the vacuum ultraviolet (VUV) region. Such gases include, but are not limited to, xenon and mixtures of xenon. Xenon is known to emit strong VUV at wavelengths of about 142 nm and about 173 nm. The VUV emitting gas excites a luminescent material 31 such as UV phosphor that may partially coat or wholly coats the interior of the plasma-shell 30. Such VUV to UV phosphors include, but are not limited to, $LaPO_4$:Pr, $YPO_4$:Pr, $Sr(Al,Mg)_{12}O_{19}$:Pr, $Ca_2P_2O_7$:Pr,Na, and $CaSO_4$:Pb. Optionally other beneficial materials may be added to at least a portion of the inner surface including materials to encourage ionization of the gas or protection of the phosphor 31. Such optional materials include, but are not limited to, MgO, diamond, carbon nanotubes, $LaB_6$ and LSM. Optional electrodes may be added to the exterior or interior of the plasma-shell 30 to concentrate charge.

Figure 4E:
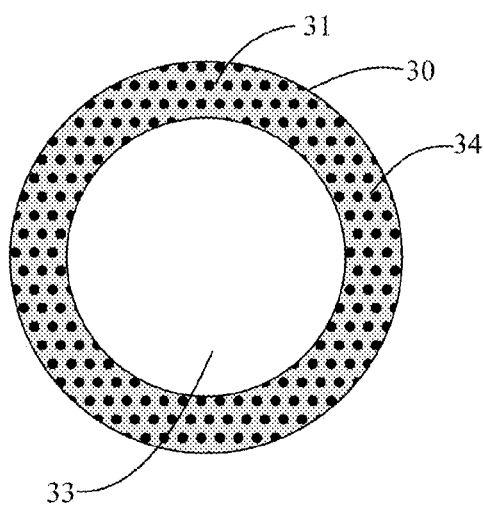
FIG. 4E shows a cross-section view of a plasma-sphere embodiment.

FIG. 4E illustrates a section 4E-4E view of the UV plasma-shell 30. The plasma-shell illustrated is a plasma-sphere. The plasma-shell 30 is comprised in whole or in part of material 34 that is transmissive to UV radiation and a luminescent material 31 such as a phosphor. Such UV transmissive materials include various transparent oxides including, but not limited to, aluminum oxide ($Al_2O_3$) also known as alumina. The plasma-shell 30 is impervious and encapsulates a gas 33 that when energized, emits energy in the vacuum ultraviolet (VUV) region. Such gases include, but are not limited to, xenon and mixtures of xenon. Xenon is known to emit strong VUV at wavelengths of about 142 nm and about 173 nm. The VUV emitting gas excites a luminescent material 31, such as a phosphor. Such VUV to UV phosphors include, but are not limited to, $LaPO_4$:Pr, $YPO_4$:Pr, $Sr(Al,Mg)_{12}O_{19}$:Pr, $Ca_2P_2O_7$:Pr,Na, and $CaSO_4$:Pb. Optionally other beneficial materials may be added to at least a portion of the inner surface including materials to encourage ionization of the gas or protection of the phosphor 31. Such optional materials include, but are not limited to, MgO, diamond, carbon nanotubes, $LaB_6$ and LSM. Optional electrodes may be added to the exterior or interior of the plasma-shell 30 to concentrate charge.

Figure 4F:
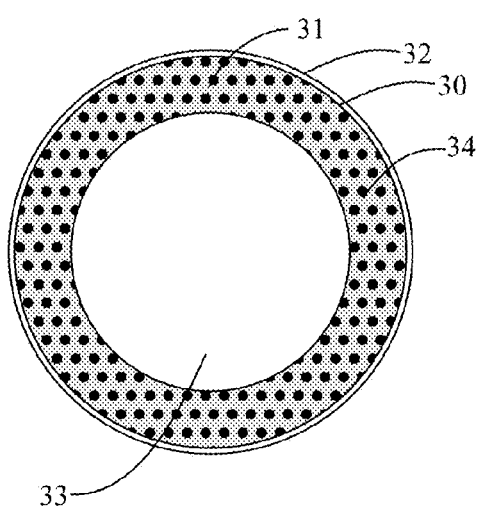
FIG. 4F shows a cross-section view of a plasma-sphere embodiment.

FIG. 4F illustrates a section 4F-4F view of the UV plasma-shell 30. The plasma-shell illustrated is a plasma-sphere. The plasma-shell 30 is comprised in whole or in part of material 34 that is transmissive to UV radiation and a luminescent material 31 such as a phosphor. The plasma-shell is coated with a thin film layer of a beneficial material 32. Such materials include, but are not limited to, titanium oxide including titanium dioxide ($TiO_2$) and titanium dioxide doped with tungsten trioxide. When titanium dioxide is exposed to UV radiation, it photocatalyzes producing a germicidal effect.

UV transmissive materials include various transparent oxides including, but not limited to, aluminum oxide including $Al_2O_3$. The plasma-shell 30 is impervious and encapsulates a gas 33 that when energized, emits energy in the vacuum ultraviolet (VUV) region. Such gases include, but are not limited to, xenon and mixtures of xenon. Xenon is known to emit strong VUV at wavelengths of about 142 nm and about 173 nm. The VUV emitting gas excites a luminescent material 31, such as a phosphor. Such VUV to UV phosphors include, but are not limited to, $LaPO_4$:Pr, $YPO_4$:Pr, $Sr(Al,Mg)_{12}O_{19}$:Pr, $Ca_2P_2O_7$:Pr,Na, and $CaSO_4$:Pb. Optionally other beneficial materials may be added to at least a portion of the inner surface including materials to encourage ionization of the gas or protection of the phosphor 31. Such optional materials include, but are not limited to, MgO, diamond, carbon nanotubes, $LaB_6$ and LSM. Optional electrodes may be added to the exterior or interior of the plasma-shell 30 to concentrate charge.

Figure 5B:
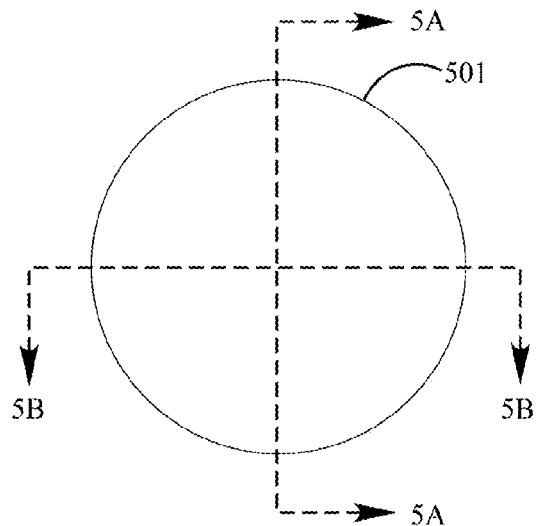
Figure 5B:
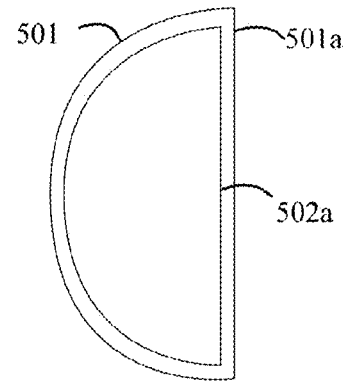
Figure 5B:
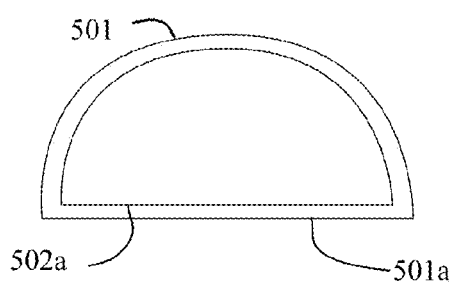

A plasma-shell in the shape of a plasma-dome is shown in FIGS. 5, 5A, and 5B. FIG. 5 is a top view of a plasma-dome showing an outer wall 501. FIG. 5A is a section 5A-5A view of FIG. 5 showing a flattened outer wall 501a and flattened inner wall 502a. FIG. 5B is a section 5B-5B view of FIG. 5.

Figure 6:
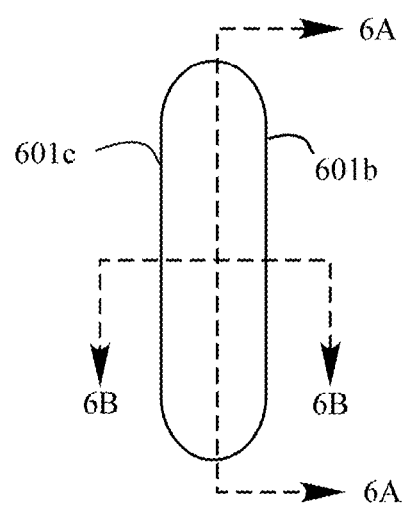
FIGS. 6, 6A, and 6B show a plasma-dome with multiple flat sides.
Figure 6A:
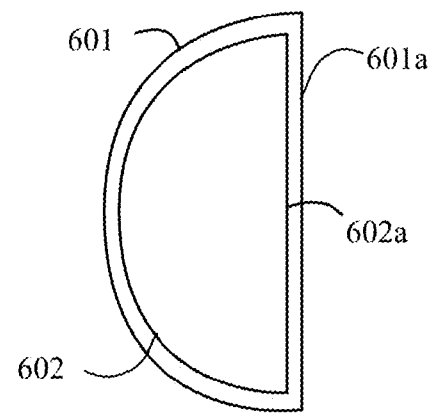
Figure 6B:
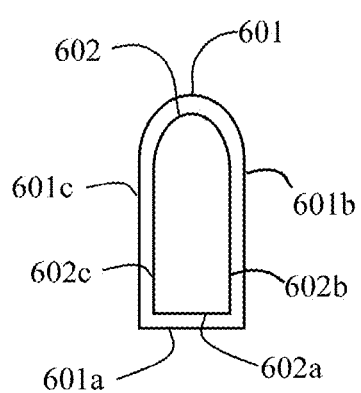

FIG. 6 is a top view of a plasma-dome with flattened outer wall 601b and 601c. FIG. 6A is a section 6A-6A view of FIG. 6 showing flattened outer wall 601a and flattened inner wall 602a with a plasma-dome having outer wall 601 and inner wall 602. FIG. 6B is a section 6B-6B view of FIG. 6.

FIGS. 7A and 7B show a plasma-shell in the shape of a plasma-disc. As illustrated in FIGS. 7A and 7B, the plasma-disc has opposing flat circular sides 701. FIG. 7A is a section 7A-7A view of FIG. 7B. FIG. 7B is a section 7B-7B view of FIG. 7A. As shown in FIG. 7A, the ends 702 are rounded and do not have corners with the inside wall surface 703 of the hollow plasma-disc.

Figure 8:
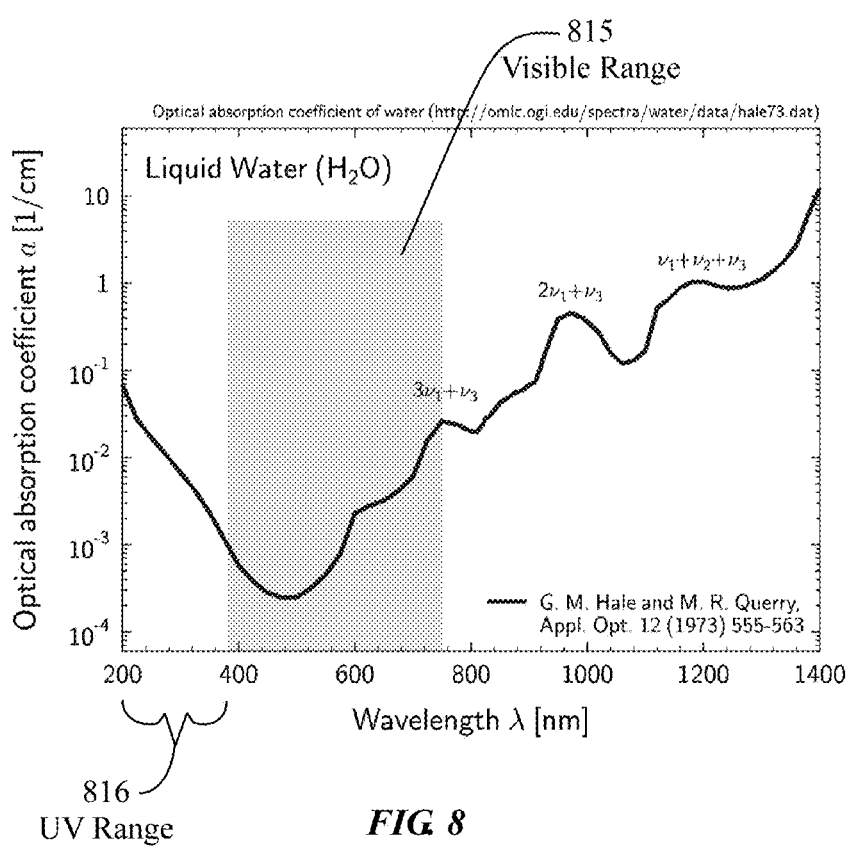
FIG. 8 shows the optical absorption rate of UV in water.

FIG. 8 shows the optical absorption rate of UV light 816 in water. UV light wavelengths 816 are well absorbed in water, whereas some wavelengths of visible light 815 are not well absorbed. For example, blue light in the 440 nm to 520 nm range is not absorbed well by water and red light in the range of 720 nm to 760 nm is well absorbed by water.

The Beer-Lambert Law is the linear relationship between absorbance and concentration of an absorber of electromagnetic radiation.

Where I is the resultant intensity of light calculated by the intensity of the incident light $I_0$ times $$I=I_0 e^{-\alpha x}$$

the Euler number e to the inverse a (absorption coefficient) times the distance the light travels through a substance such as water. The absorption coefficient α is the inverse distance along which the intensity of light drops by a factor of e=2.718, and is measured in inverse centimeters.

Therefore, in order for the intensity UV light to be decreased by a factor of e by a liquid such as water, it must travel a distance of 1 meter.

Plasma-shells fabricated with different phosphors and different gases, same phosphors and different gases, or different phosphors and the same gases to emit different UV wavelengths may be used in the same UV emission device.

Figure 9B:
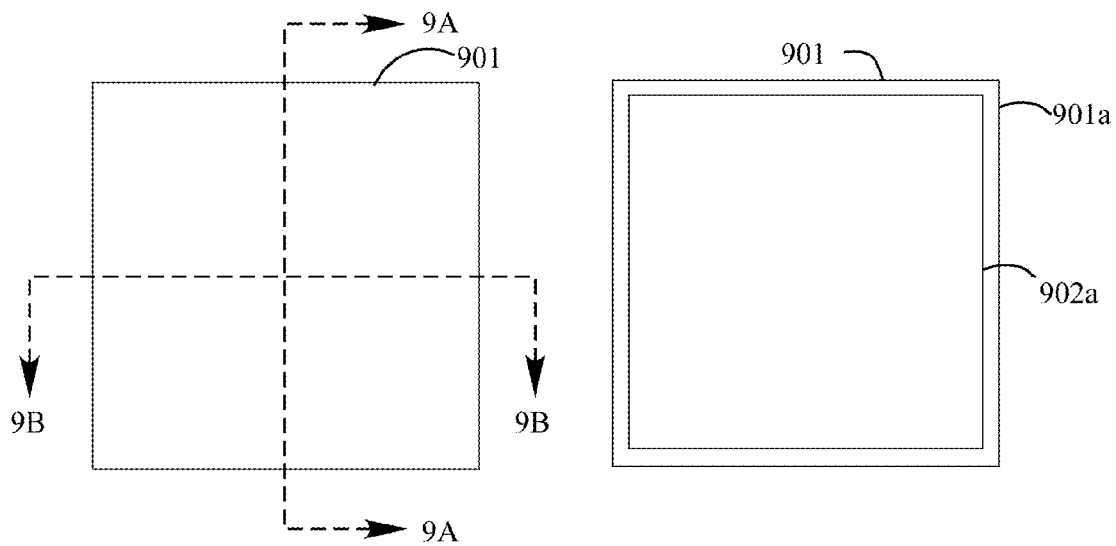
Figure 9B:
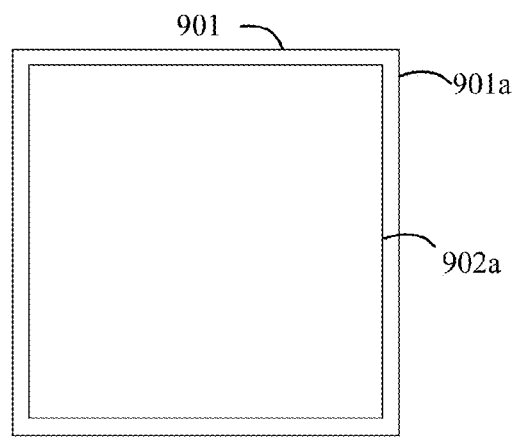

FIG. 9A is a section 9A-9A view of FIG. 9 with flat, parallel sides 901, inside wall surface 902a, and outer wall surface 901a.

FIG. 9B is a section 9B-9B view of FIG. 9 with flat, parallel sides 901, inside wall surface 902a, and outer wall surface 901a.

Figure 10:
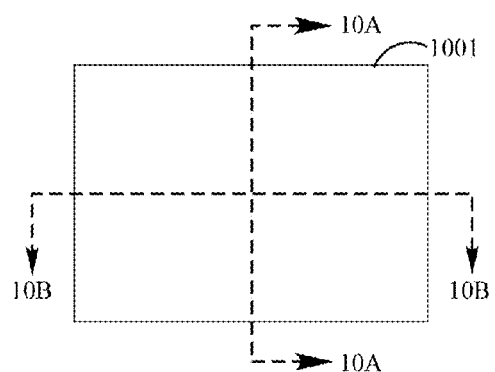
FIGS. 10, 10A, and 10B show a plasma-cuboid.
Figure 10A:
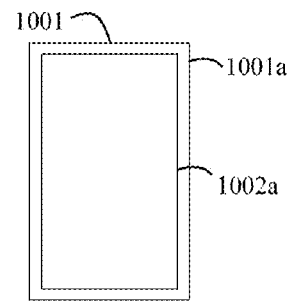
Figure 10B:
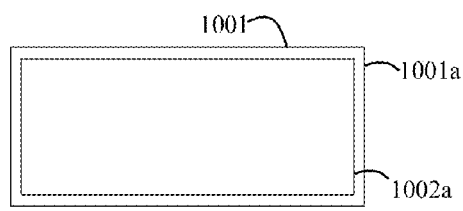

FIGS. 10, 10A, and 10B show a plasma-shell in the shape of a plasma-cuboid. As illustrated in FIG. 10, the plasma-cuboid has opposing flat, parallel sides 1001.

FIG. 10A is a section 10A-10A view of FIG. 10 with flat, parallel sides 1001, inside wall surface 1002a, and outer wall surface 1001a.

FIG. 10B is a section 10B-10B view of FIG. 10 with flat, parallel sides 1001, inside wall surface 1002a, and outer wall surface 1001a.

Figure 11:
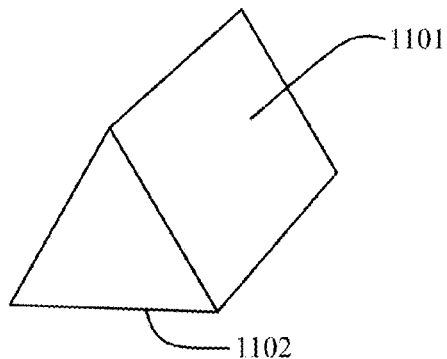
FIGS. 11, 11A, 11B, and 11C show a right equilateral triangular plasma-prism.

FIGS. 11, 11A, 11B, and 11C show a plasma-shell in the shape of a right triangular plasma-prism. As illustrated in FIG. 11, the right triangular plasma-prism has flat sides 1101 and base 1102.

Figure 11A:
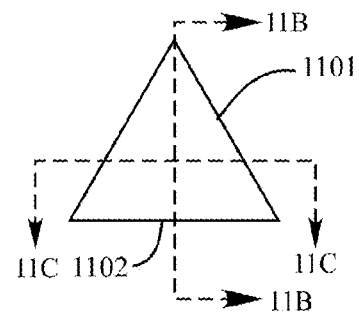

FIG. 11A shows an end view of the right triangular plasma-prism with sides 1101 and base 1102.

Figure 11B:
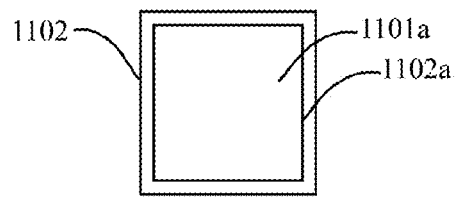

FIG. 11B is a section 11B-11B view of FIG. 11A with sides 1101, inner side surface 1101a, bases 1102 and inner base surface 1102a.

Figure 11C:
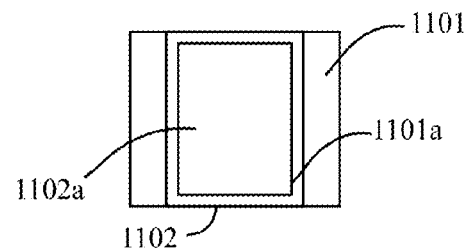

FIG. 11C is a section 11C-11C view of FIG. 11A with sides 1101, inner side surface 1101a, bases 1102 and inner base surface 1102a.

Figure 12:
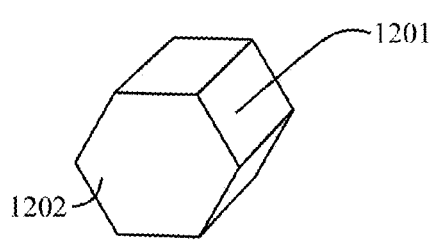
FIGS. 12, 12A, 12B, and 12C show a right hexagonal plasma-prism.

FIGS. 12, 12A, 12B, and 12C show a plasma-shell in the shape of a right hexagonal plasma-prism. As illustrated in FIG. 12, the right hexagonal plasma-prism has flat sides 1201 and base 1202.

Figure 12A:
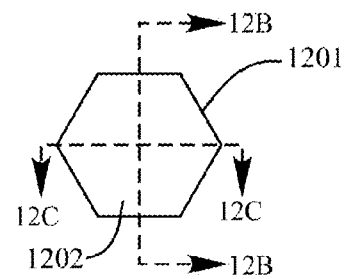

FIG. 12A shows an end view of the right hexagonal plasma-prism with sides 1201 and base 1202.

Figure 12B:
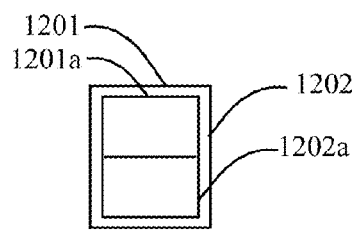

FIG. 12B is a section 12B-12B view of FIG. 12A with sides 1201, inner side surface 1201a, bases 1202 and inner base surface 1202a.

Figure 12C:
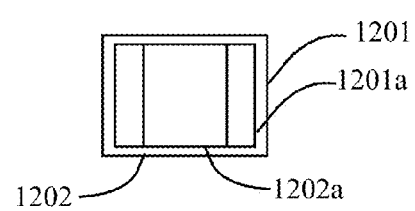

FIG. 12C is a section 12C-12C view of FIG. 12A with sides 1201, inner side surface 1201a, bases 1202 and inner base surface 1202a.

Figure 13:
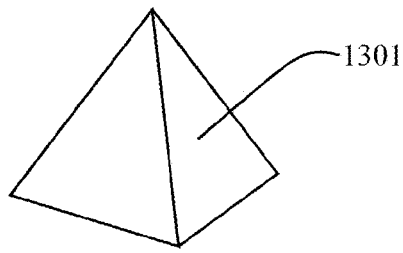
FIGS. 13, 13A, 13B, and 13C show a right triangular plasma-pyramid.

FIGS. 13, 13A, 13B, and 13C show a plasma-shell in the shape of a right triangular plasma-pyramid. As illustrated in FIG. 13, the right triangular plasma-pyramid has sides 1301 and base 1302.

Figure 13A:
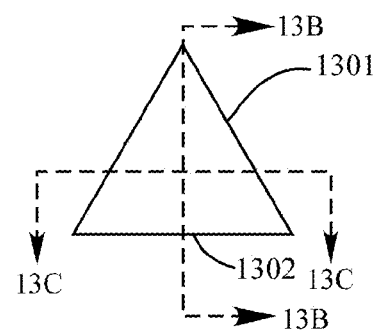

FIG. 13A shows an end view of the right triangular plasma-pyramid with sides 1301 and base 1302.

Figure 13B:
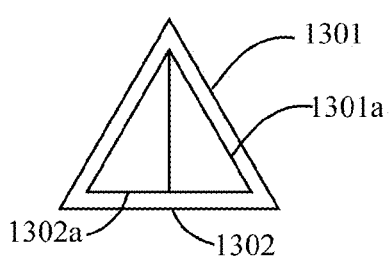

FIG. 13B is a section 13B-13B view of FIG. 13A with sides 1301, inner side surface 1301a, bases 1302 and inner base surface 1302a.

Figure 13C:
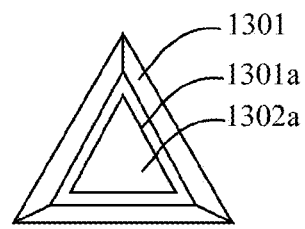

FIG. 13C is a section 13C-13C view of FIG. 13A with sides 1301, inner side surface 1301a, bases 1302 and inner base surface 1302a.

Figure 14:
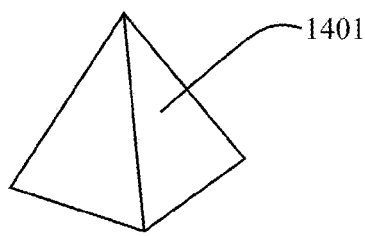
FIGS. 14, 14A, 14B, and 14C show a right square plasma-pyramid.

FIGS. 14, 14A, 14B, and 14C show a plasma-shell in the shape of a right square plasma-pyramid. As illustrated in FIG. 14, the right square plasma-pyramid has sides 1401 and base 1402.

Figure 14A:
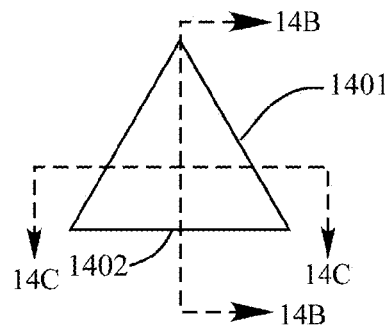

FIG. 14A shows an end view of the right square plasma-pyramid with sides 1401 and base 1402.

Figure 14B:
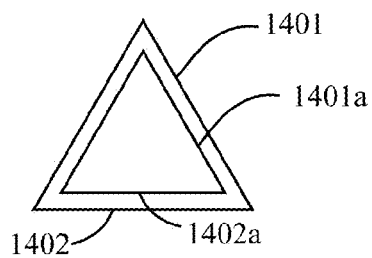

FIG. 14B is a section 14B-14B view of FIG. 14A with sides 1401, inner side surface 1401a, bases 1402 and inner base surface 1402a.

Figure 14C:
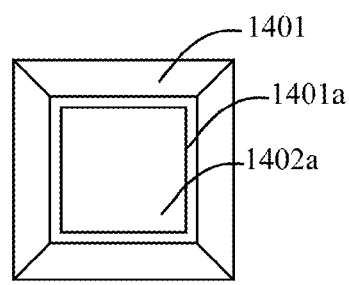

FIG. 14C is a section 14C-14C view of FIG. 14A with sides 1401, inner side surface 1401a, bases 1402 and inner base surface 1402a.

Figure 15:
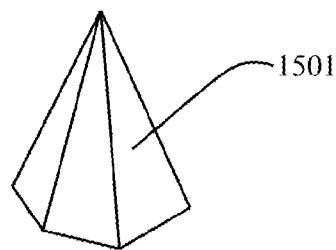
FIGS. 15, 15A, 15B, and 15C show a right hexagonal plasma-pyramid.

FIGS. 15, 15A, 15B, and 15C show a plasma-shell in the shape of a right hexagonal plasma-pyramid. As illustrated in FIG. 15, the right hexagonal plasma-pyramid has sides 1501 and base 1502.

Figure 15A:
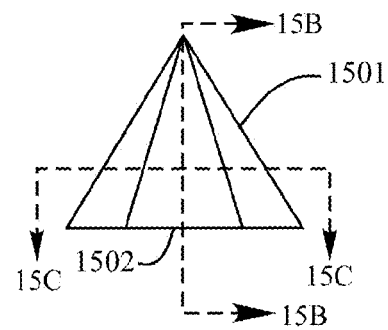

FIG. 15A shows an end view of the right hexagonal plasma-pyramid with sides 1501 and base 1502.

Figure 15B:
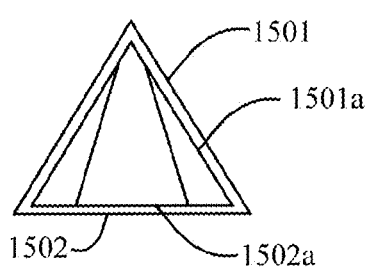

FIG. 15B is a section 15B-15B view of FIG. 15A with sides 1501, inner side surface 1501a, bases 1502 and inner base surface 1502a.

Figure 15C:
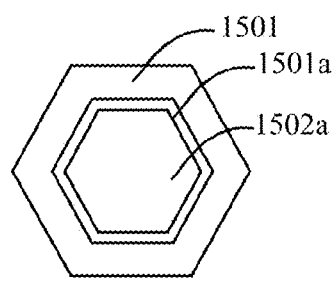

FIG. 15C is a section 15C-15C view of FIG. 15A with sides 1501, inner side surface 1501a, bases 1502 and inner base surface 1502a.

Figure 16:
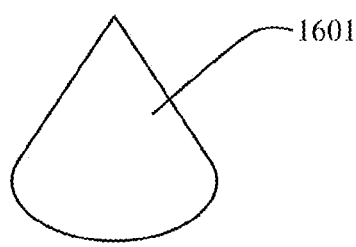
FIGS. 16, 16A, 16B, and 16C show a right circular plasma-cone.

FIGS. 16, 16A, 16B, and 16C show a plasma-shell in the shape of a right circular plasma-cone. As illustrated in FIG. 16, the right circular plasma-cone has sides 1501 and base 1502.

Figure 16A:
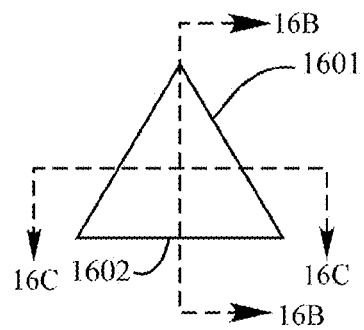

FIG. 16A shows an end view of the right circular plasma-cone with sides 1601 and base 1602.

Figure 16B:
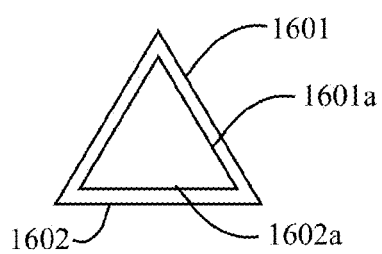

FIG. 16B is a section 16B-16B view of FIG. 16A with sides 1601, inner side surface 1601a, bases 1602 and inner base surface 1602a.

Figure 16C:
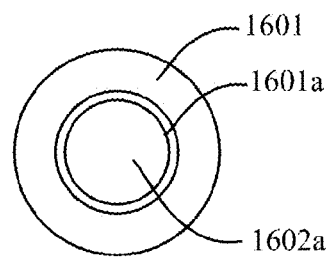

FIG. 16C is a section 16C-16C view of FIG. 16A with sides 1601, inner side surface 1601a, bases 1602 and inner base surface 1602a.

Figure 17:
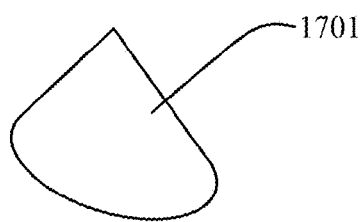
FIGS. 17, 17A, 17B, and 17C show a right elliptical plasma-cone.

FIGS. 17, 17A, 17B, and 17C show a plasma-shell in the shape of a right elliptical plasma-cone. As illustrated in FIG. 17, the right elliptical plasma-cone has sides 1701 and base 1702.

Figure 17A:
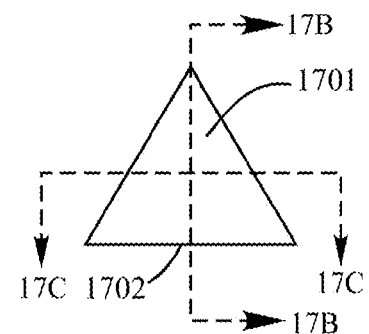

FIG. 17A shows an end view of the right elliptical plasma-cone with sides 1701 and base 1702.

Figure 17B:
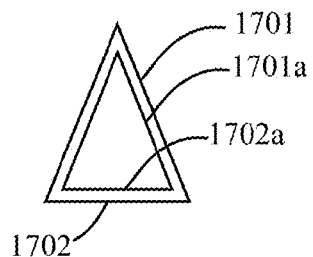

FIG. 17B is a section 17B-17B view of FIG. 17A with sides 1701, inner side surface 1701a, bases 1702 and inner base surface 1702a.

Figure 17C:
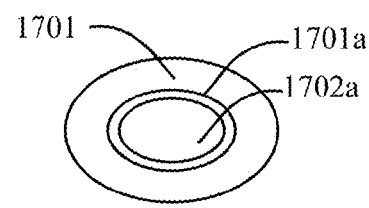

FIG. 17C is a section 17C-17C view of FIG. 17A with sides 1701, inner side surface 1701a, bases 1702 and inner base surface 1702a.

Figure 18:
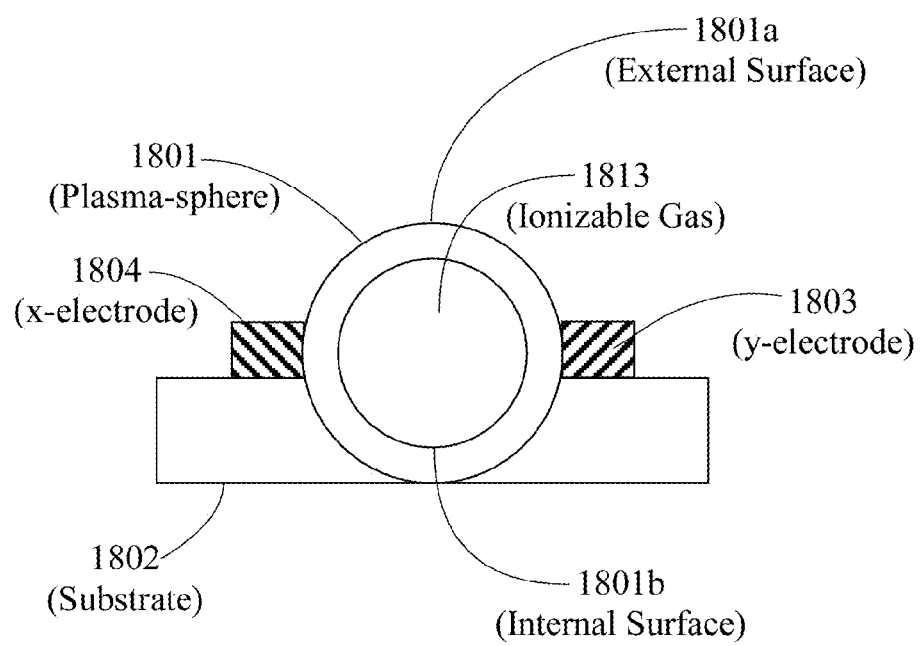
FIG. 18 shows a plasma-sphere located on a substrate with a x-electrode and y-electrode.

FIG. 18 shows a hollow plasma-sphere 1801 with external surface 1801a and internal surface 1801b located within a substrate 1802 with x-electrode 1804 and y-electrode 1803. The plasma-sphere 1801 contains ionizable gas 1813.

Figure 19A:
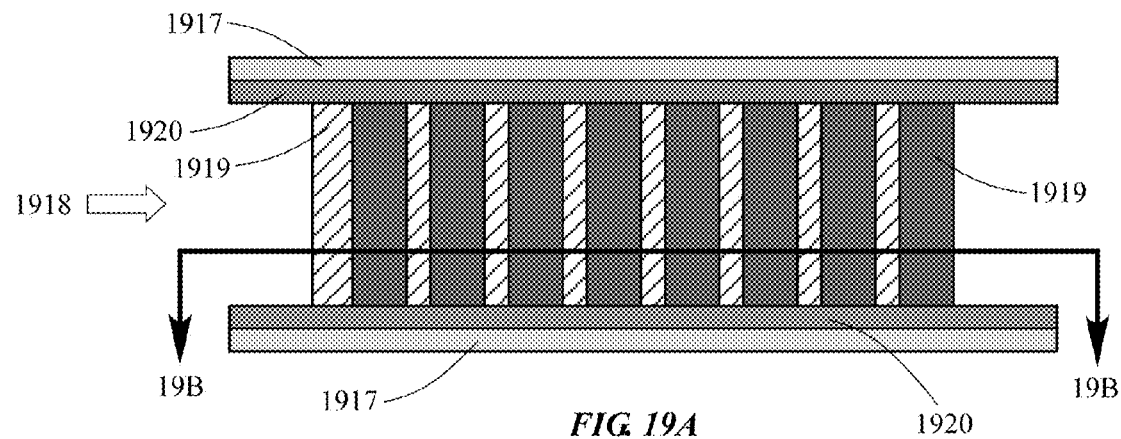
FIG. 19A shows a side view of plasma-tubes between two conductive plates.

FIG. 19A This "sandwich" configuration illustrates a water and/or air purification system consistent with this invention. It consists of two parallel conductive plates 1917 which together supply a voltage across UV plasma-tubes 1919. The plasma-tubes may be optionally coated with beneficial material such as $TiO_2$. Material 1920 insulates electrical current on conducting plate from water or gas 1918 and also affixes the plasma-tubes into position.

Figure 19B:
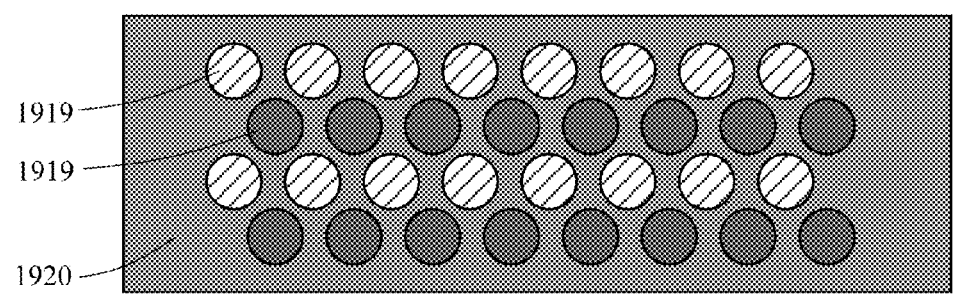
FIG. 19B shows a section 19B-19B view of plasma-tubes between two conductive plates.

FIG. 19B is a section 19B-19B view of the configuration in FIG. 19A which shows the plasma-tubes 1919 in staggered rows. In the case of water or air purification, this creates turbulence causing more water or air to be exposed to the UV light source. In this configuration, plasma-tubes and/or plasma-shells of any size and/or geometric shape are contemplated ranging from about 1 mm to about 15 mm in length. A preferred length range is about 4 mm to about 8 mm. Widths and depth can rage from about 0.5 mm to about 8 mm. A preferred range is about 2 mm to 4 mm. Although described with reference to UV-emitting shells for use in purification applications, plasma-tubes that emit light other than UV may be used including shells that emit visible and/or IR light. Suitable material for the parallel plats includes metal or other conductive material alone or in conjunction with a base material such as FR4, glass, and plastic.

Figure 20A:
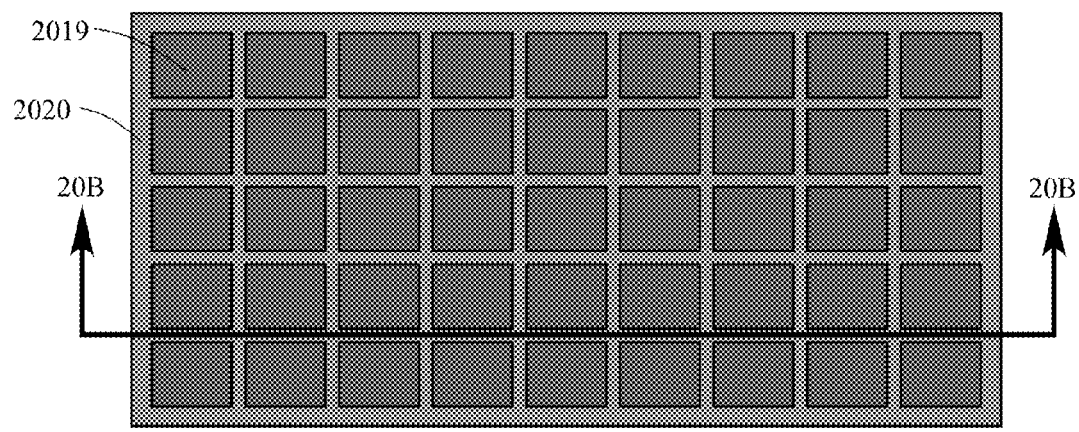
FIG. 20A shows a top view of plasma-cuboids on a single substrate.
Figure 20B:
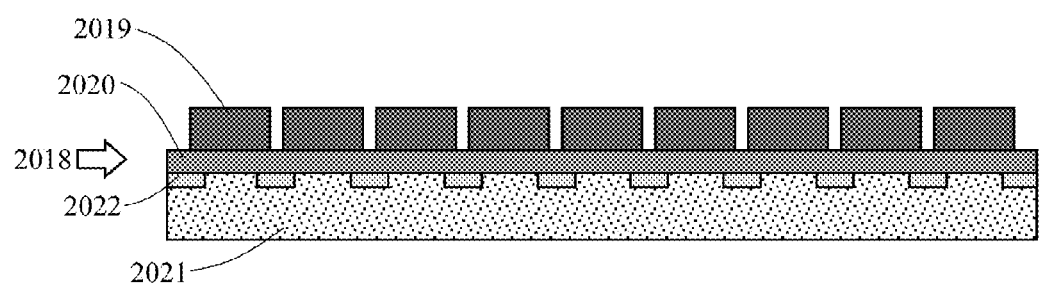
FIG. 20B shows a section 20B-20B view of plasma-cuboids on a single substrate.

FIG. 20A shows this "open-faced sandwich configuration" illustrates an illumination device consistent with the invention. In this configuration, plasma-shells 2019 are positioned on the surface of or embedded into a single substrate 2021. Material 2020 insulates electrical current from water or gas 2018 and also affixes UV plasma-shells 2019 into position. Electrodes 2022 provide a voltage potential across the bottom of the plasma-shells.

This embodiment is preferred for providing a uniform homogenous light source. Although this application can be used to purify or treat liquid and gas, such an embodiment is especially useful for photocatalytic applications. It is also of use in medical applications. Although described with reference to UV emitting plasma-shells, the plasma-shells may emit visible and IR light.

In another embodiment, electrodes 2022 are at the same potential and an external ground potential is used to bias the plasma-shells 2019. For example plasma-shells that 2019 are in direct contact with a grounded object will energize.

Figure 21:
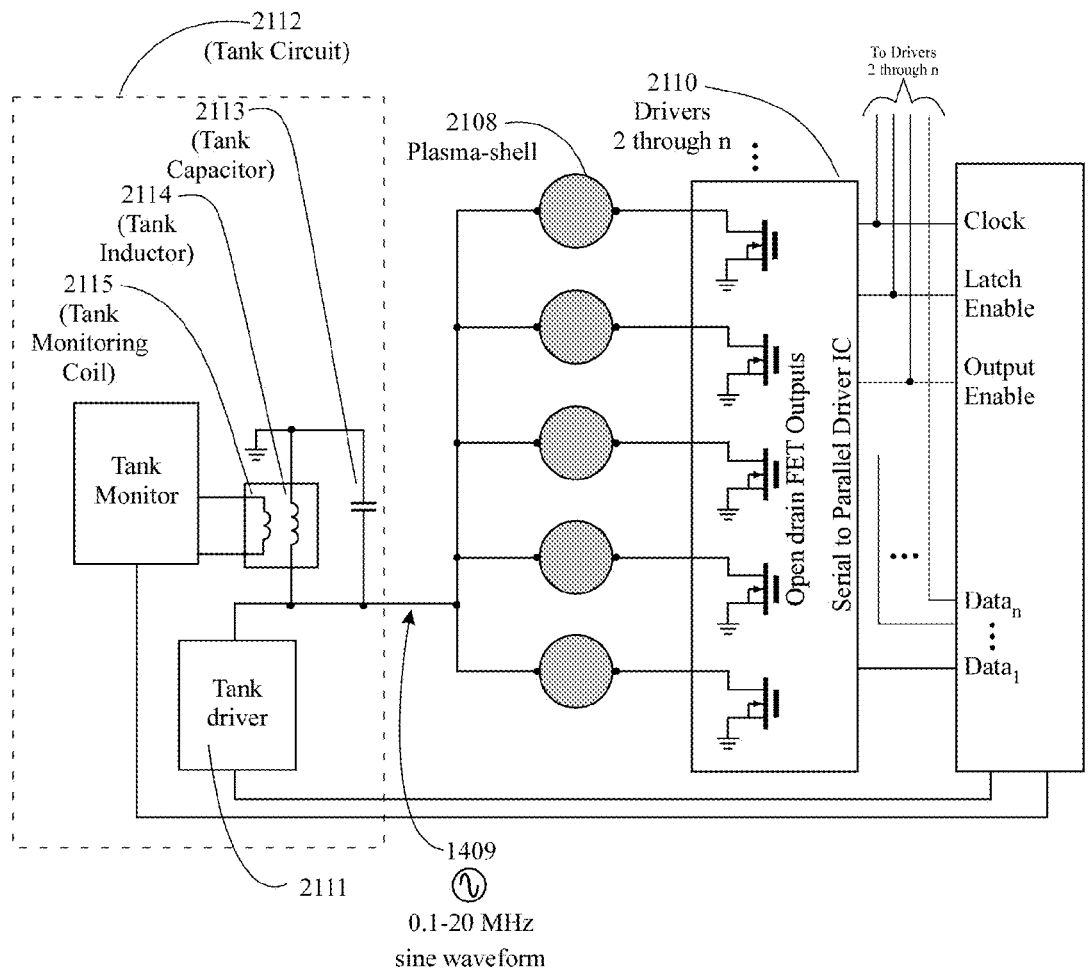
FIG. 21 is a schematic diagram showing electronic circuitry for driving an array of plasma-shells or plasma-tubes.

FIG. 21 is a schematic diagram showing electronic circuitry suitable for operating an array of plasma-shells 2108. The plasma-shells 2108 produce high luminance when driven with high frequency and high voltage excitation. The high frequency circuitry provides a sine waveform 2109 to the plasma-shell array. The principle circuit element is an open drain, low capacitance, high voltage IC output 2110 in series with each plasma-shell 2108 and the high voltage common AC driving source. When an IC output 2110 is ON, the AC voltage from the source is imposed across an individual plasma-shell 2108, which has enough amplitude to quickly light (ionize) the plasma-shell 2108. When the output 2110 is OFF most of the source voltage appears across the low capacitance open drain output and therefore the plasma-shell turns OFF. This full parallel drive to all plasma-shells simultaneously synchronized with the 1 MHz high voltage power source provides digital control of the AC plasma-shells without the requirement of discharge memory. Thus 500 levels of gray at 2,000 hertz to 10,000 levels of gray at 100 hertz is achieved.

The electronic drive circuit includes a high frequency (1.2 MHz) L-C tank circuit 2112 with a drive transistor 2111. This drive transistor 2111 may be a single transistor that pulls the waveform to a positive or negative peak or a pair of transistors, one transistor that pulls the waveform to a positive peak and one transistor that pulls the waveform to a negative peak. The single transistor or pair of transistors are energy efficient because these transistors supply charge or energy to the tank capacitor 2113 and/or tank inductor 2114 only when there is low voltage across the transistor supplying the charge or energy. The tank circuit 2112 provides a very efficient use of electrical energy without the need for additional energy recovery circuitry. The prior art energy recovery circuitry increases electronic complexity and is also less efficient than the parallel tank circuit drive.

Figure 22:
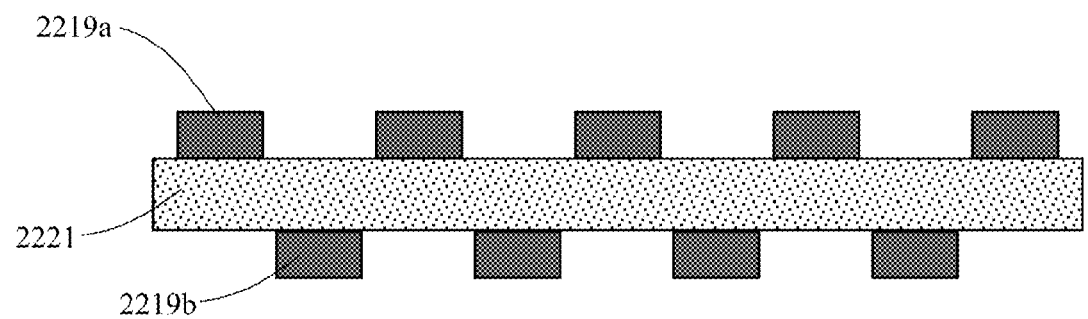
FIG. 22 shows a side view of a single substrate with cuboid plasma-shells on both sides of the substrate.

FIG. 22 shows a side view of a single substrate 2221 with cuboid plasma-shells 2219a and 2219b on both sides of the substrate 2221.

Figure 23:
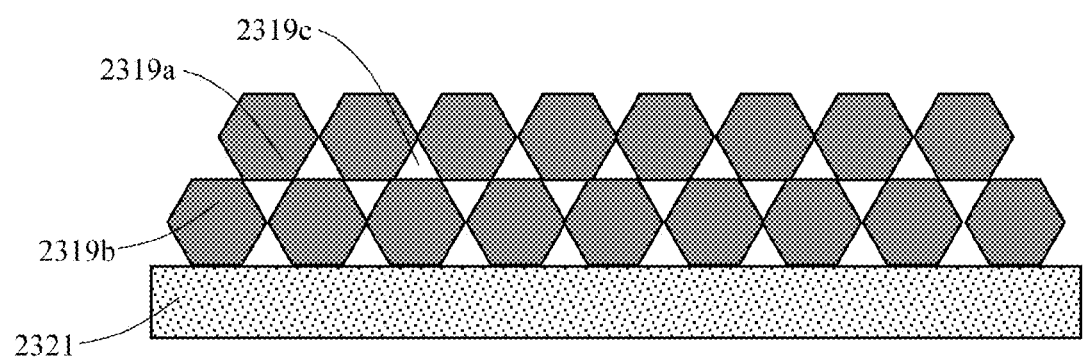
FIG. 23 shows an end view of a single substrate with right hexagonal plasma-prisms stacked on one side of a substrate.

FIG. 23 shows an end view of a single substrate 2321 with right hexagonal plasma-prisms 2319a and 2219b stacked on one side of the substrate 2221. By offsetting the right hexagonal plasma-prisms 2319a and 2319b, a space 2319c is formed which allows for fluid to pass between the plasma-prisms, and provides a greater surface area for the fluid to be exposed to the ultraviolet light. The shells may be stacked on either side of the substrate 2321.

Figure 24:
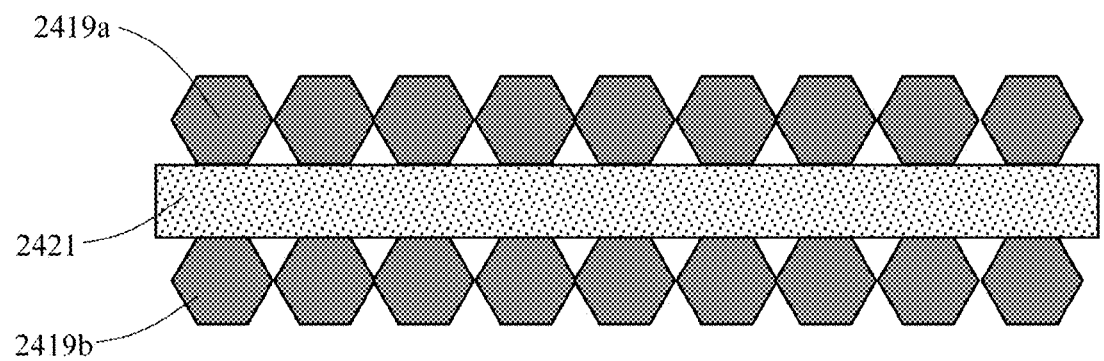
FIG. 24 shows an end view of a single substrate with right hexagonal plasma-shells on both sides of the substrate.

FIG. 24 shows an end view of a single substrate 2421 with right hexagonal plasma-shells 2419a and 2419b on both sides of the substrate 2421.

Figure 25:
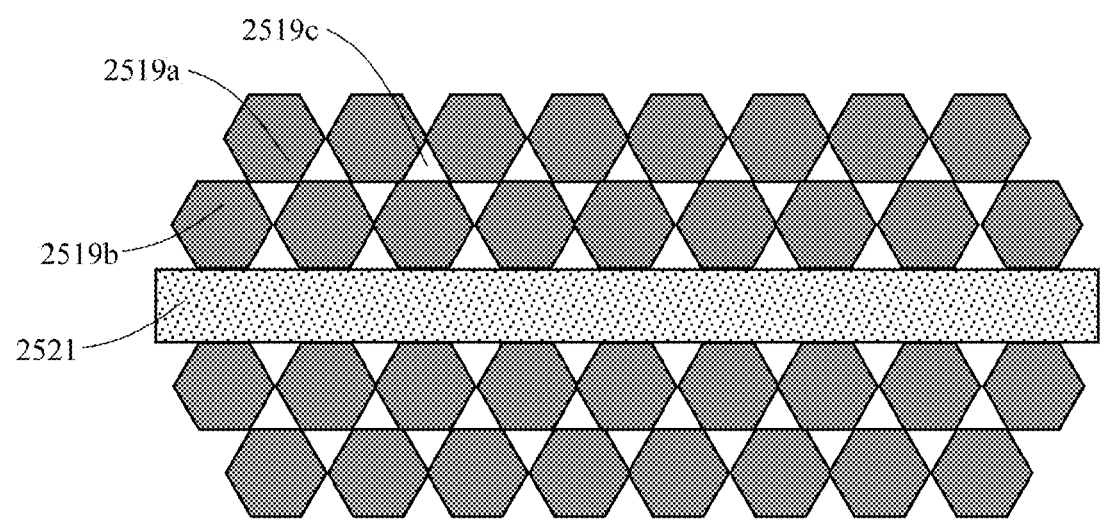
FIG. 25 shows an end view of a single substrate with right hexagonal plasma-prisms stacked on both sides of a substrate.

FIG. 25 shows an end view of a single substrate 2521 with right hexagonal plasma-prisms 2519a, 2519b stacked on both sides of a substrate 2521. By offsetting the right hexagonal plasma-prisms 2519a and 2519b, a space 2519c is formed which allows for fluid to pass between the plasma-prisms, and provides a greater surface area for the fluid to be exposed to the ultraviolet light. The shells may be stacked on either side of the substrate 2321.

PRIOR ART

Ultraviolet Sterilizers

UV sterilizers are found in the prior art in many different applications. U.S. Pat. No. 3,906,236 (Callahan), U.S. Pat. No. 4,772,795 (Sakurai et al.), U.S. Pat. No. 4,983,411 (Tanaka et al.), U.S. Pat. No. 5,166,528 (Le Vay), U.S. Pat. No. 6,656,424 (Deal), all incorporated herein by reference, use UV light to sterilize or purify a solid or a surface.

U.S. Pat. No. 2,636,991 (Postell), U.S. Pat. No. 4,798,702 (Tucker), U.S. Pat. No. 6,087,774 (Makayama et al.), and U.S. Pat. No. 6,916,452 (Rix et al.), all incorporated herein by reference, use UV light to sterilize or purify a liquid.

U.S. Pat. No. 3,634,025 (Landry), U.S. Pat. No. 4,033,719 (Conn et al.), U.S. Pat. No. 4,969,991 (Valadez), U.S. Pat. No. 5,445,729 (Monroe et al.), and U.S. Pat. No. 5,785,845 (Colaiano), all incorporated herein by reference, use UV light to sterilize or purify drinking water.

U.S. Pat. No. 6,685,826 (James), U.S. Pat. No. 6,709,574 (James), U.S. Pat. No. 7,431,848 (James), and U.S. Design Pat. No. 350,181 (MacNeal), all incorporated herein by reference, use UV light to sterilize or purify water in swimming pools, hot tubs, spas, ponds, and aquariums.

U.S. Pat. No. 6,570,173 (Kunkel et al.) and U.S. Pat. No. 7,160,441 (Gannon et al.), all incorporated herein by reference, use UV light to sterilize or purify sewage water.

U.S. Pat. No. 3,418,069 (Decupper), U.S. Pat. No. 3,576,593 (Cicirello), U.S. Pat. No. 7,380,627 (Huang et al.), and U.S. Design Pat. No. 358,637 (Boehme) and 485,364 (Lee), all incorporated herein by reference, use UV light to sterilize or purify a gas or air.

Ultraviolet Curing

The plasma-shell structure of this invention may be used to generate UV to induce UV curing, for example as discussed in U.S. Pat. No. 4,563,589 (Scheffer), U.S. Pat. No. 6,207,118 (Gaven et al.), and U.S. Pat. No. 8,458,923 (Mackinnon et al.) and U.S. Patent Application Publication No. 2006/0233501 (Sampson), and 2015/0132973 (Hung et al.), all incorporated herein by reference.

Devices used to cure materials utilizing ultraviolet light are well known in the prior art. Including U.S. Pat. No. 4,563,589 (Scheffer) which discloses a device used for curing photopolymerizable products.

U.S. Pat. No. 6,207,118 (Gaven et al.) discloses a mobile ultraviolet substrate coating curing device which is adapted to cure substrate coatings in inaccessible areas, such as floor corners, walls, overhangs, edges and ceilings.

U.S. Pat. No. 8,458,923 (Mackinnon et al.) discloses a portable floor curing device.

U.S. Patent Application Publication 2006/0233501 (Sampson)) discloses a curing apparatus comprising a plurality of light emitting areas each being operable to emit ultraviolet radiation.

U.S. Patent Application Publication 2015/0132973 (Hung et al.) discloses an ultraviolet curing apparatus including a chamber, a gas flow generator, and an ultraviolet lamp.

Ultraviolet Catalysts

Devices utilizing ultraviolet radiation as a catalyst for chemical reactions include U.S. Patent Application Publication 2008/0135399 (Mukaddam et al) discloses an apparatus and method for using an ultraviolet laser system to decompose selected chemical substances in water.

U.S. Pat. No. 6,627,268 (Fair et al.) discloses an ion-induced, UV-induced, and electron-induced sequential chemical vapor deposition (CVD) processes are disclosed where an ion flux, a flux of ultra-violet radiation, or an electron flux, respectively, is used to induce the chemical reaction in the process.

U.S. Patent Application Publication 2004/024779 (Selvamanickam et al.) discloses a high-throughput, ultraviolet (UV) assisted metalorganic chemical vapor deposition (MOCVD) system for the manufacture of HTS-coated tapes.

Ultraviolet Inducing of Chemical Reactions

The plasma-shell structure of this invention may be used to generate UV to induce a chemical reaction, for example as disclosed in U.S. Pat. No. 6,627,268 (Fair et al.) and U.S. Pat. No. 7,897,215 (Fair et al.) and U.S. Patent Application Publication No. 2004/024779 (Selvamanickam et al.) and 2007/0249128 (Kim et al.), all incorporated herein by reference.

U.S. Pat. No. 7,897,215 (Fair et al.) discloses an Ion-induced, UV-induced, and electron-induced sequential chemical vapor deposition (CVD) processes are disclosed where an ion flux, a flux of ultra-violet radiation, or an electron flux, respectively, is used to induce the chemical reaction in the process.

U.S. Patent Application Publication 2007/0249128 (Kim et al.) discloses a method of vapor deposition in which dielectric layers are formed on a substrate by performing Subatmospheric Chemical Vapor Deposition (SACVD) of ozone-tetraethoxysilane ($O_3$-TEOS) to form a layer of $O_3$-TEOS on the substrate, and treating the layer of $O_3$-TEOS with ultraviolet (UV) radiation.

Methods of Producing Plasma-Shells

Any suitable method or process may be used to produce the gas-filled plasma-shells. Methods and processes for the production of hollow shells or plasma-shells are known in the prior art. Plasma-shells have been formed from glass, ceramic, metal, plastic, and other inorganic and organic materials. Varying methods and processes for producing shells and plasma-shells have been disclosed and practiced in the prior art. Some of the prior art methods for producing plasma-shells are disclosed hereafter.

One method used to produce hollow glass plasma-shells comprises incorporating a blowing gas into the lattice of a glass while in frit form. The blowing gases typically include $SO_2$, $CO_2$, and $H_2O$. The frit is heated and glass bubbles are formed by the in-permeation of the blowing gas. Plasma-shells formed by this method have diameters ranging from about 5 µm to approximately 5,000 µm.

Methods of manufacturing glass frit for forming hollow plasma-shells are disclosed by U.S. Pat. No. 4,017,290 (Budrick et al.) and U.S. Pat. No. 4,021,253 (Budrick et al.). Budrick et al. '290 discloses a process whereby occluded material gasifies to form the hollow plasma-shell. Hollow plasma-shells are disclosed in U.S. Pat. No. 5,500,287 (Henderson) and U.S. Pat. No. 5,501,871 (Henderson). The hollow plasma-shells are formed in Henderson '287 by dissolving a permeant gas (or gases) into glass frit particles. The gas permeated frit particles are then heated at a high temperature sufficient to blow the frit particles into hollow plasma-shells containing the permeant gases. The gases may be subsequently out-permeated and evacuated from the hollow plasma-shell as described in step D in column 3 of Henderson '287.

U.S. Pat. No. 4,257,798 (Hendricks et al.) incorporated herein by reference, discloses a method for manufacturing small hollow glass spheres. The gases include argon, krypton, xenon, bromine, DT, hydrogen, deuterium, helium, hydrogen, neon, and carbon dioxide. Other Hendricks patents for the manufacture of glass spheres include U.S. Pat. Nos. 4,133,854 and 4,186,637, incorporated herein by reference.

Plasma-shells are also produced as disclosed in U.S. Pat. No. 4,415,512 (Torobin), incorporated herein by reference. This method by Torobin comprises forming a film of molten glass across a blowing nozzle and applying a blowing gas at a positive pressure on the inner surface of the film to blow the film and form an elongated cylinder shaped liquid film of molten glass. An inert entraining fluid is directed over and around the blowing nozzle at an angle to the axis of the blowing nozzle so that the entraining fluid dynamically induces a pulsating or fluctuating pressure at the opposite side of the blowing nozzle in the wake of the blowing nozzle. The continued movement of the entraining fluid produces asymmetric fluid drag forces on a molten glass cylinder, which forces closed and detached the elongated cylinder from the coaxial blowing nozzle. Surface tension forces acting on the detached cylinder form the latter into a spherical shape, which is rapidly cooled and solidified by cooling means to form a glass plasma-shell.

In one embodiment of the above method for producing the plasma-shells, the ambient pressure external to the blowing nozzle is maintained at a super atmospheric pressure. The ambient pressure external to the blowing nozzle is such that it substantially balances, but is slightly less than the blowing gas pressure. Such a method is disclosed by U.S. Pat. No. 4,303,432 (Torobin) and WO 8000438A1 (Torobin), both incorporated herein by reference. The plasma-shells may also be produced using a centrifuge apparatus and method as disclosed by U.S. Pat. No. 4,303,433 (Torobin) and WO8000695A1 (Torobin), both incorporated herein by reference.

Other methods for forming plasma-shells of glass, ceramic, metal, plastic, and other materials are disclosed in other Torobin patents including U.S. Pat. Nos. 5,397,759; 5,225,123; 5,212,143; 4,793,980; 4,777,154; 4,743,545; 4,671,909; 4,637,990; 4,582,534; 4,568,389; 4,548,196; 4,525,314; 4,363,646; 4,303,736; 4,303,732; 4,303,731; 4,303,603; 4,303,431; 4,303,730; 4,303,729; and 4,303,061, all incorporated herein by reference.

U.S. Pat. No. 3,607,169 (Coxe) discloses an extrusion method in which a gas is blown into molten glass and individual shells are formed. As the shells leave the chamber, they cool and a portion of the gas is trapped inside. U.S. Pat. No. 4,349,456 (Sowman), incorporated herein by reference, discloses a process for making ceramic metal oxide plasma-shells by blowing a slurry of ceramic and highly volatile organic fluid through a coaxial nozzle. As the liquid dehydrates, gelled microcapsules are formed. These microcapsules are recovered by filtration and then dried and fired to form plasma-shells. Prior to firing, the microcapsules are sufficiently porous such that, if placed in a vacuum during the firing process, the gases are removed and the resulting plasma-shells will generally be impermeable to ambient gases. The shells formed with this method may be filled with a variety of gases and pressurized from near vacuums to above atmosphere. This is a suitable method for producing plasma-shells. Apparatus to prepare discrete hollow shells is disclosed in U.S. Pat. No. 7,730,746 (Pavliscak et al.), incorporated herein by reference.

U.S. Patent Application Publication 2002/0004111 (Matsubara et al.), incorporated herein by reference, discloses a method of preparing hollow glass plasma-shells by adding a combustible liquid (kerosene) to a material containing a foaming agent. Methods for forming plasma-shells are also disclosed in U.S. Pat. No. 3,848,248 (MacIntyre), U.S. Pat. No. 3,998,618 (Kreick et al.), and U.S. Pat. No. 4,035,690 (Roeber), discussed above and incorporated herein by reference. Methods of manufacturing hollow plasma-shells are disclosed in U.S. Pat. No. 3,794,503 (Netting), U.S. Pat. No. 3,796,777 (Netting), U.S. Pat. No. 3,888,957 (Netting), and U.S. Pat. No. 4,340,642 (Netting et al.), all incorporated herein by reference.

Other prior art methods for forming plasma-shells are disclosed in the prior art including U.S. Pat. No. 3,528,809 (Farnand et al.), U.S. Pat. No. 3,975,194 (Farnand et al.), U.S. Pat. No. 4,025,689 (Kobayashi et al.), U.S. Pat. No. 4,211,738 (Genis), U.S. Pat. No. 4,307,051 (Sargeant et al.), U.S. Pat. No. 4,569,821 (Duperray et al.) U.S. Pat. No. 4,775,598 (Jaeckel), and U.S. Pat. No. 4,917,857 (Jaeckel et al.), all incorporated herein by reference. These references disclose a number of methods which comprise an organic core such as naphthalene or a polymeric core such as foamed polystyrene which is coated with an inorganic material such as aluminum oxide, magnesium, refractory, carbon powder, and the like. The core is removed by pyrolysis, sublimation, or decomposition and the inorganic coating sintered at an elevated temperature to form a sphere or plasma-shell. Farnand et al. '809 discloses the production of hollow metal spheres by coating a core material such as naphthalene or anthracene with metal flakes such as aluminum or magnesium. The organic core is sublimed at room temperature over 24 to 48 hours. The aluminum or magnesium is then heated to an elevated temperature in oxygen to form aluminum oxide or magnesium oxide. The core may also be coated with a metal oxide such as aluminum oxide and reduced to metal. The resulting hollow spheres are used for thermal insulation, plastic filler, and bulking of liquids such as hydrocarbons.

Farnand ('194) discloses a similar process comprising polymers dissolved in naphthalene including polyethylene and polystyrene. The core is sublimed or evaporated to form hollow spheres or microballoons. Kobayashi et al. '689 discloses the coating of a core of polystyrene with carbon powder. The core is heated and decomposed and the carbon powder heated in argon at 3000° C. to obtain hollow porous graphitized spheres. Genis '738 discloses the making of lightweight aggregate using a nucleus of expanded polystyrene pellet with outer layers of sand and cement. Sargeant et al. '051 discloses the making of lightweight refractories by wet spraying core particles of polystyrene with an aqueous refractory coating such as clay with alumina, magnesia, and/or other oxides. The core particles are subject to a tumbling action during the wet spraying and fired at 1730° C. to form porous refractory. Duperray et al. '821 discloses the making of a porous metal body by suspending metal powder in an organic foam which is heated to pyrolyze the organic and sinter the metal. Jaeckel '598 and Jaeckel et al. '857 disclose the coating of a polymer core particle such as foamed polystyrene with metals or inorganic materials followed by pyrolysis on the polymer and sintering of the inorganic materials to form the sphere. Both disclose the making of metal spheres such as copper or nickel spheres which may be coated with an oxide such as aluminum oxide. Jaeckel et al. '857 further discloses a fluid bed process to coat the core.

Geometric Shape

The gas-filled plasma-shells may be of any suitable hollow geometric body including a sphere, disc, dome, or other geometric shape. Combinations of shells of different geometric shape may be used.

Plasma-Shell Materials

The gas-filled plasma-shell may be constructed of any suitable material including glass, ceramic, plastic, metal, metalloids, and so forth. It is contemplated that the plasma-shell may be made of suitable inorganic compounds of metals and/or metalloids, including mixtures or combinations thereof. Contemplated inorganic compounds include the oxides, carbides, nitrides, nitrates, silicates, silicides, aluminates, phosphates, sulphates, sulfides, borates, and borides.

The metals and/or metalloids are selected from lithium, sodium, potassium, rubidium, cesium, magnesium, calcium, strontium, barium, scandium, yttrium, lanthanum, cerium, praseodymium, neodymium, promethium, samarium, europium, gadolinium, terbium, erbium, actinium, thorium, protactinium, uranium, neptunium, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, copper, silver, zinc, cadmium, boron, aluminum, gallium, indium, thallium, carbon, silicon, germanium, tin, lead, phosphorus, arsenic, antimony and bismuth.

Suitable inorganic materials include magnesium oxide(s), aluminum oxide(s), zirconium oxide(s), and silicon carbide(s) such as MgO, $Al_2O_3$, $ZrO_2$, $SiO_2$, and/or SiC.

In one embodiment, the plasma-shell is composed wholly or in part of one or more borides of one or more members of Group IIIB of the Periodic Table and/or the rare earths including both the Lanthanide Series and the Actinide Series of the Periodic Table. Contemplated Group IIIB borides include scandium boride and yttrium boride. Contemplated rare earth borides of the Lanthanides and Actinides include lanthanum boride, cerium boride, praseodymium boride, neodymium boride, gadolinium boride, terbium boride, actinium boride, and thorium boride.

In one embodiment, the plasma-shell is composed wholly or in part of one or more Group IIIB and/or rare earth hexaborides with the Group IIIB and/or rare earth element being one or more members selected from Sc, Y, La, Ce, Pr, Nd, Sm, Eu, Gd, Tb, Dy, Ho, Yb, Ac, Th, Pa, and U. Examples include lanthanum hexaboride, cerium hexaboride, and gadolinium hexaboride.

Rare earth borides, including rare earth hexaboride compounds, and methods of preparation are disclosed in U.S. Pat. No. 3,258,316 (Tepper et al.), U.S. Pat. No. 3,784,677 (Versteeg et al.), U.S. Pat. No. 4,030,963 (Gibson et al.), U.S. Pat. No. 4,260,525 (Olsen et al.), U.S. Pat. No. 4,999,176 (Iltis et al.), U.S. Pat. No. 5,238,527 (Otani et al.), U.S. Pat. No. 5,336,362 (Tanaka et al.), U.S. Pat. No. 5,837,165 (Otani et al.), and U.S. Pat. No. 6,027,670 (Otani et al.), all incorporated herein by reference.

Group IIA alkaline earth borides are contemplated including borides of Mg, Ca, Ba, and Sr. In one embodiment, there is used a material containing trivalent rare earths and/or trivalent metals such as La, Ti, V, Cr, Al, Ga, and so forth having crystalline structures similar to the perovskite structure, for example as disclosed in U.S. Pat. No. 3,386,919 (Forrat), incorporated herein by reference.

The plasma-shell may also be composed of or contain carbides, borides, nitrides, silicides, sulfides, oxides and other compounds of metals and/or metalloids of Groups IV and V as disclosed and prepared in U.S. Pat. No. 3,979,500 (Sheppard et al.), incorporated herein by reference. Compounds including borides of Group IVB metals such as titanium, zirconium, and hafnium and Group VB metals such as vanadium, niobium, and tantalum are contemplated. In one embodiment, the plasma-shell is made of fused particles of glass, ceramic, glass ceramic, refractory, fused silica, quartz, or like amorphous and/or crystalline materials including mixtures of such. The ceramic material may be selected based on its transmissivity to light after firing. This includes selecting ceramic material with various optical cutoff frequencies to produce various colors. One material contemplated for this application is aluminum oxide. Aluminum oxide is transmissive from the UV range to the IR range. Because it is transmissive in the UV range, luminescent materials such as phosphors excited by UV may be applied to the exterior of an aluminum oxide to produce various colors. The application of the phosphor to the exterior of the plasma-shell may be executed by any suitable means before or after the plasma-shell is positioned on or in the substrate. Several layers or coatings of phosphors, each of a different composition, can be applied to the exterior of the plasma-shell.

In one embodiment, the plasma-shell is made of an aluminate silicate or contains a layer of aluminate silicate. When the ionizable gas mixture contains helium, the aluminate silicate is especially beneficial in preventing the escape of helium. It is also contemplated that the plasma-shell may be made of lead silicates, lead phosphates, lead oxides, borosilicates, alkali silicates, aluminum oxides, and pure vitreous silica.

The plasma-shell may be made in whole or in part from one or more materials such as magnesium oxide having a sufficient Townsend coefficient. These include inorganic compounds of magnesium, calcium, strontium, barium, gallium, lead, aluminum, boron, and the rare earths especially lanthanum, cerium, actinium, and thorium. The contemplated inorganic compounds include oxides, carbides, nitrides, nitrates, silicates, silicides, aluminates, phosphates, sulphates, sulfides, borates, borides, and other inorganic compounds of the above and other elements.

The plasma-shell may also contain or be partially or wholly constructed of luminescent materials such as inorganic and/or organic phosphor(s). The phosphor may be a continuous or discontinuous layer or coating of inorganic and/or organic substance on the interior or exterior of the plasma-shell. Inorganic and/or organic luminescent particles may also be introduced inside the plasma-shell or embedded within the plasma-shell. Inorganic and/or organic luminescent quantum dots may also be incorporated into the plasma-shell.

Ionizable Gas

The hollow gas-filled plasma-shell contains one or more ionizable gas components that are ionized and/or discharged by an energy source. The gas may be selected to emit photons in the visible, IR, and/or UV spectrum during ionization and/or gas discharge. The photons may be utilized to excite a luminescent material.

As used herein, gas means one or more gas components. In the practice of this invention, the gas is typically selected from a mixture of the rare gases of neon, argon, xenon, krypton, helium, and/or radon. The rare gas may be a Penning gas mixture. Other contemplated gases include nitrogen, $CO_2$, CO, mercury, halogens, excimers, oxygen, hydrogen, and mixtures thereof. Isotopes of the above and other gases are contemplated. These include isotopes of helium such as helium-3, isotopes of hydrogen such as deuterium (heavy hydrogen), tritium ($T^3$) and DT, isotopes of the rare gases such as xenon-129, and isotopes of oxygen such as oxygen-18. Other isotopes include deuterated gases such as deuterated ammonia ($ND_3$) and deuterated silane ($SiD_4$). In one embodiment, a two-component gas mixture (or composition) is used such as a mixture of neon and argon, neon and xenon, neon and helium, neon and krypton, argon and xenon, argon and krypton, argon and helium, xenon and krypton, xenon and helium, and krypton and helium. Specific two-component gas mixtures (compositions) include about 5% to 90% atoms of argon with the balance xenon. Another two-component gas mixture is a mother gas of neon containing 0.05% to 15% atoms of xenon, argon, and/or krypton. This can also be a three-component gas, four-component gas, or five-component gas by using quantities of an additional gas or gases selected from xenon, argon, krypton, and/or helium. In another embodiment, a three-component ionizable gas mixture is used such as a mixture of argon, xenon, and neon wherein the mixture contains at least 5% to 80% atoms of argon, up to about 15% xenon, and the balance neon. The xenon is present in a minimum amount sufficient to maintain the Penning effect. Such a mixture is disclosed in U.S. Pat. No. 4,926,095 (Shinoda et al.), incorporated herein by reference. Other three-component gas mixtures include argon-helium-xenon, krypton-neon-xenon, and krypton-helium-xenon for example as disclosed in U.S. Pat. Nos. 5,510,678 and 5,559,403 issued to Sakai et al., both incorporated herein by reference.

U.S. Pat. No. 4,081,712 (Bode et al.), incorporated herein by reference, discloses the addition of helium to a gaseous medium of 90% to 99.99% atoms of neon and 10% to 0.01% atoms of argon, xenon, and/or krypton. In one embodiment, there is used a high concentration of helium with the balance selected from one or more gases of neon, argon, xenon, and nitrogen as disclosed in U.S. Pat. No. 6,285,129 (Park) incorporated herein by reference. Mercury may also be added to the rare gases as disclosed in U.S. Pat. No. 4,041,345 (Sahni), incorporated herein by reference.

A high concentration of xenon may also be used with one or more other gases as disclosed in U.S. Pat. No. 5,770,921 (Aoki et al.), incorporated herein by reference. Pure neon may be used and the shells operated using the architecture disclosed by U.S. Pat. No. 3,958,151 (Yano) discussed above and incorporated herein by reference. In some embodiments, a radioactive gas such as radon may be used alone or in combination with other gases. A variety of other gases is contemplated.

Excimers

Excimer gases may also be used as disclosed in U.S. Pat. Nos. 4,549,109 and 4,703,229 issued to Nighan et al., both incorporated herein by reference. Nighan et al. '109 and '229 disclose the use of excimer gases formed by the combination of halides with inert gases. The halides include fluorine, chlorine, bromine, and iodine. The inert gases include helium, xenon, argon, neon, krypton, and radon. Excimer gases may emit red, blue, green, or other color light in the visible range or light in the invisible range. The excimer gases may be used alone or in combination with phosphors. U.S. Pat. No. 6,628,088 (Kim et al.), incorporated herein by reference, also discloses excimer gases for a PDP.

Gas Pressure

The gas pressure inside of the hollow gas-filled plasma-shell may be equal to or less than atmospheric pressure or may be equal to or greater than atmospheric pressure. In another embodiment, the gas pressure inside of the plasma-shell is equal to or less than atmospheric, about 20 to 760 Torr, typically about 150 to about 450 Torr. In one embodiment, the gas pressure inside of the plasma-shell is equal to or greater than atmospheric. Depending upon the structural strength of the plasma-shell, the pressure above atmospheric may be about 1 to 250 atmospheres (about 760 to 190,000 Torr) or greater. Higher gas pressures increase the luminous efficiency of the UV sterilizer. The gas pressure is selected to allow efficient ionization and/or gas discharge. In one embodiment, the gas pressure is selected to allow the gas to ionize or discharge when a low voltage is applied.

Electrodes

One or more electrodes may be connected to each plasma-shell to efficiently couple the energy source to the plasma-shell. Depending on the application, it may be necessary to insulate the electrode. For example, if the system is being used to purify water, it is desirable to insulate the electrodes from the water.

In one embodiment, one or more hollow gas-filled plasma-shells containing the ionizable gas are interconnected to one or more other plasma-shells. The electrodes may contact the surface of the plasma-shell, extend through the plasma-shell so as to be in direct contact with the ionizable gas inside the plasma-shell, or be in close proximity of the plasma-shells. In accordance with one embodiment, the contact of the electrode to the plasma-shell is augmented with a supplemental electrically conductive bonding substance applied to each plasma-shell, or to each electrode, so as to form an electrically conductive pad connection to the electrodes. A dielectric substance may also be used in lieu of, or in addition to, the conductive substance.

Each electrode pad may partially cover an outside surface of the plasma-shell. The electrodes and pads are any geometric shape or configuration. In one embodiment the electrodes are opposing arrays of electrodes, one array of electrodes being transverse or orthogonal to an opposing array of electrodes. The electrode arrays can be parallel, zig zag, serpentine, or like pattern. The use of split or divided electrodes is contemplated as disclosed in U.S. Pat. No. 3,603,836 (Grier) and U.S. Pat. No. 3,701,184 (Grier), incorporated herein by reference. Apertured electrodes may be used as disclosed in U.S. Pat. No. 6,118,214 (Marcotte) and U.S. Pat. No. 5,411,035 (Marcotte) and U.S. Patent Application Publication 2004/0001034 (Marcotte), all incorporated herein by reference.

A flat plasma-shell surface is particularly suitable for connecting electrodes to the plasma-shell. If one or more electrodes are connected to the bottom of a plasma-shell, a flat bottom surface is desirable. Likewise, if one or more electrodes are connected to the top or sides of the plasma-shell, it is advantageous for the connecting surface of such top or sides to be flat. In a matrix of plasma-shells, the electrodes in each opposing transverse array are transverse to the electrodes in the opposing array so that each electrode in each array forms a crossover with an electrode in the opposing array, the two arrays thereby forming a multiplicity of crossovers. Each crossover of two opposing electrodes forms a discharge cell. At least one hollow plasma-shell containing ionizable gas is positioned at the intersection of at least two opposing electrodes. When an appropriate voltage potential is applied to an opposing pair of electrodes, the ionizable gas inside of the plasma-shell at the crossover is energized and a gas discharge occurs. Photons of light in the visible and/or invisible range are emitted by the gas discharge.

Electrode Materials

The electrodes are of any suitable conductive metal or alloy including gold, platinum, silver, aluminum, nickel, copper, chrome, or chrome-copper-chrome. If an electrode transparent to visible light is required on the viewing surface, this is typically indium tin oxide (ITO) or tin oxide with a conductive side or edge bus bar of silver. Other conductive bus bar materials may be used such as gold, aluminum, nickel, or chrome-copper-chrome. For improved electrical contact, the electrodes may partially cover the external surface of the plasma-shell.

The electrodes may contain a secondary electron emission (Townsend coefficient) material such as a coating for secondary electron emission material such as magnesium oxide. There also may be a protective coating over the electrode, which can be a secondary electron emission material such as magnesium oxide, gadolinium hexaboride or lanthanum hexaboride as disclosed in U.S. Pat. No. 7,145,612 (Sakai et al.), incorporated herein by reference. The rare earth hexaborides are good electron-emitting materials as disclosed in U.S. Pat. No. 5,837,165 (Otani et al.), incorporated herein by reference.

In one embodiment using two electrodes, one electrode such as an anode is composed of lanthanum hexaboride and the other electrode such as a cathode is platinum, for example, as disclosed in U.S. Pat. No. 5,643,692 (Ohmi). In some embodiments, one or more of the conductors or electrodes connected to the plasma-shell is composed of or contains a rare earth oxide such as cerium oxide or lanthanum oxide. Also magnesium diboride may be used as a conductor or electrode. In another embodiment, an anode is composed of lanthanum hexaboride and the cathode is platinum, for example, as disclosed in U.S. Pat. No. 5,643,692 (Ohmi).

The materials disclosed above for the plasma-shell materials and/or secondary electron emission materials are also suitable, especially the borides for electrode materials. In addition, magnesium tetraboride and titanium boride are contemplated.

The electrodes may be applied to the shells and/or supporting substrate by thin film methods such as vapor phase deposition, E-beam evaporation, sputtering, conductive doping, electro-plating, etc. or by thick film methods such as screen printing, ink jet printing, etc.

Electrically Conductive Bonding Substance

In one embodiment, one or more conductors or electrodes are electrically connected to each gas-filled plasma-shell with an electrically conductive bonding substance. This may be applied to an exterior surface of the shell, to an electrode, and/or to a substrate surface. In one embodiment, the conductive bonding substance it is applied to both the shell and the electrode.

The electrically conductive bonding substance can be any suitable inorganic or organic material including compounds, mixtures, dispersions, pastes, liquids, cements, and adhesives. In one embodiment, the electrically conductive bonding substance is an organic substance with conductive filler material. Contemplated organic substances include adhesive monomers, dimers, trimers, polymers and copolymers of materials such as polyurethanes, polysulfides, silicones, and epoxies. A wide range of other organic or polymeric materials may be used. Contemplated conductive filler materials include conductive metals or metalloids such as silver, gold, platinum, copper, chromium, nickel, aluminum, and carbon. The conductive filler may be of any suitable size and form such as particles, powder, agglomerates, or flakes of any suitable size and shape. It is contemplated that the particles, powder, agglomerates, or flakes may comprise a non-metal, metal, or metalloid core with an outer layer, coating, or film of conductive metal. Some specific embodiments of conductive filler materials include silver-plated copper beads, silver-plated glass beads, silver particles, silver flakes, gold-plated copper beads, gold-plated glass beads, gold particles, gold flakes, and so forth. In one particular embodiment of this invention there is used an epoxy filled with 60% to 80% silver by weight.

Examples of electrically conductive bonding substances are known in the art. The disclosures including the compositions of the following references are incorporated herein by reference. U.S. Pat. No. 3,412,043 (Gilliland) discloses an electrically conductive composition of silver flakes and resinous binder. U.S. Pat. No. 3,983,075 (Marshall et al.) discloses a copper filled electrically conductive epoxy. U.S. Pat. No. 4,247,594 (Shea et al.) discloses an electrically conductive resinous composition of copper flakes in a resinous binder. U.S. Pat. No. 4,552,607 (Frey) and U.S. Pat. No. 4,670,339 (Frey) disclose a method of forming an electrically conductive bond using copper gas-filled plasma-shells in an epoxy. U.S. Pat. No. 4,880,570 (Sanborn et al.) discloses an electrically conductive epoxy-based adhesive selected from the amine curing modified epoxy family with a filler of silver flakes. U.S. Pat. No. 5,183,593 (Durand et al.) discloses an electrically conductive cement comprising a polymeric carrier such as a mixture of two epoxy resins and filler particles selected from silver agglomerates, particles, flakes, and powders. The filler may be silver-plated particles such as inorganic spheroids. Other noble metals and non-noble metals such as nickel are disclosed. U.S. Pat. No. 5,298,194 (Carter et al.) discloses an electrically conductive adhesive composition comprising a polymer or copolymer of polyolefins or polyesters filled with silver particles. U.S. Pat. No. 5,575,956 (Hermansen et al.) discloses electrically conductive, flexible epoxy adhesives comprising a polymeric mixture of a polyepoxide resin and an epoxy resin filled with conductive metal powder, flakes, or non-metal particles having a metal outer coating. The conductive metal is a noble metal such as gold, silver, or platinum. Silver-plated copper beads and silver-plated glass beads are also disclosed. U.S. Pat. No. 5,891,367 (Basheer et al.) discloses a conductive epoxy adhesive comprising an epoxy resin cured or reacted with selected primary amines and filled with silver flakes. The primary amines provide improved impact resistance. U.S. Pat. No. 5,918,364 (Kulesza et al.) discloses substrate bumps or pads formed of electrically conductive polymers filled with gold or silver. U.S. Pat. No. 6,184,280 (Shibuta) discloses an organic polymer containing hollow carbon microfibers and an electrically conductive metal oxide powder.

In another embodiment, the electrically conductive bonding substance is an organic substance without a conductive filler material. Examples of electrically conductive bonding substances are known in the art. The disclosures including the compositions of the following references are incorporated herein by reference. Electrically conductive polymer compositions are disclosed in U.S. Pat. No. 5,917,693 (Kono et al.), U.S. Pat. No. 6,096,825 (Garnier), and U.S. Pat. No. 6,358,438 (Isozaki et al.). The electrically conductive polymers disclosed above may also be used with conductive fillers. In some embodiments, organic ionic materials such as calcium stearate may be added to increase electrical conductivity as disclosed in U.S. Pat. No. 6,599,446 (Todt et al.), incorporated herein by reference. In one embodiment, the electrically conductive bonding substance is luminescent, for example as disclosed in U.S. Pat. No. 6,558,576 (Brielmann et al.), incorporated herein by reference.

U.S. Pat. No. 5,645,764 (Angelopoulos et al.) discloses electrically conductive pressure sensitive polymers without conductive fillers. Examples of such polymers include electrically conductive substituted and unsubstituted polyanilines, substituted and unsubstituted polyparaphenylenes, substituted and unsubstituted polyparaphenylene vinylenes, substituted and unsubstituted polythiophenes, substituted and unsubstituted polyazines, substituted and unsubstituted polyfuranes, substituted and unsubstituted polypyrroles, substituted and unsubstituted polyselenophenes, substituted and unsubstituted polyphenylene sulfides and substituted and unsubstituted polyacetylenes formed from soluble precursors. Blends of these polymers are suitable for use as are copolymers made from the monomers, dimers, or trimers used to form these polymers.

Radio Frequency

The plasma-shells or plasma-tubes may be operated with radio frequency (RF). The RF is used to sustain the plasma discharge. RF may also be used to operate the plasma-shells or plasma-tubes with a positive column discharge. The use of RF in a PDP is disclosed in the following prior art, all incorporated herein by reference. U.S. Pat. No. 6,271,810 (Yoo et al.), U.S. Pat. No. 6,340,866 (Yoo), U.S. Pat. No. 6,473,061 (Lim et al.), U.S. Pat. No. 6,476,562 (Yoo et al.), U.S. Pat. No. 6,483,489 (Yoo et al.), U.S. Pat. No. 6,501,447 (Kang et al.), U.S. Pat. No. 6,605,897 (Yoo), U.S. Pat. No.

6,624,799 (Kang et al.), U.S. Pat. No. 6,661,394 (Choi), and U.S. Pat. No. 6,794,820 (Kang et al.).

Photon Exciting of Luminescent Substance

A luminescent substance such as an inorganic and/or organic luminescent phosphor may be located on all or part of the external surface of the shells and/or on all or part of the internal surface of the shells. The phosphor may comprise particles dispersed or floating within the gas. The luminescent material may be incorporated into the plasma-shell.

In one embodiment, a layer, coating, or particles of an inorganic and/or organic luminescent substance such as phosphor is located on part or all of the exterior wall surfaces of the plasma-shell. The photons of light pass through the plasma-shell or wall(s) of the plasma-shell and excite the organic or inorganic photoluminescent phosphor located outside of the plasma-shell. In some embodiments of this invention, the emitted light may not be visible to the human eye. Up-conversion or down-conversion phosphors may be used.

The phosphor may be located on the side wall(s) of a channel, trench, barrier, rib, groove, cavity, well, hollow or like structure that supports the plasma-shell. In some embodiments, the wall(s) are made of phosphor. The gas discharge in the plasma-shell within the channel, trench, barrier, groove, cavity, well or hollow produces photons and excites the inorganic and/or organic phosphor such that the phosphor emits light in a range visible to the human eye or invisible light in the UV and/or IR range.

Inorganic and/or organic phosphor may be located on the wall(s) or side(s) of barriers that form the channel, trench, groove, cavity, well, or hollow as disclosed in U.S. Pat. No. 5,793,158 (Wedding) and U.S. Pat. No. 5,661,500 (Shinoda et al.), incorporated herein by reference. Phosphor may also be located on the bottom of the channel, trench or groove as disclosed by Wedding '158 or Shinoda et al. '500 or on the bottom cavity, well, or hollow as disclosed by U.S. Pat. No. 4,827,186 (Knauer et al.). The plasma-shells are positioned within or along the walls of a channel, barrier, trench, groove, cavity, well or hollow so as to be in close proximity to the phosphor such that photons from the gas discharge within the plasma-shell cause the phosphor along the wall(s), side(s) or at the bottom of the channel, barrier, trenches groove, cavity, well, or hollow, to emit light in the visible and/or invisible range.

The inorganic and/or organic luminescent substance may be located on the external surface and is excited by photons from the gas discharge inside the plasma-shell. The phosphor may also be selected to emit light in non-visible ranges of the spectrum. Optical filters may be selected and matched with different phosphors. In this embodiment, the outside surface is at least partially covered with phosphor that emits light in the visible or invisible range when excited by photons from the gas discharge within the plasma-shell. The phosphor may emit light in the visible, UV, and/or IR range.

In one embodiment, phosphor is dispersed and/or suspended within the ionizable gas inside each plasma-shell. In such embodiment, the phosphor particles are sufficiently small such that most of the phosphor particles remain suspended within the gas and do not precipitate or otherwise substantially collect on the inside wall or inner side of the plasma-shell. The average diameter of the dispersed and/or suspended phosphor particles is less than about 1 micron, typically less than 0.1 micron. Larger particles can be used depending on the size of the plasma-shell. The phosphor particles may be introduced by means of a fluidized bed.

Organic Luminescent Substances

Organic luminescent substances may be used alone or in combination with inorganic luminescent substances. Contemplated combinations include mixtures and/or selective layers of organic and inorganic substances. In accordance with one embodiment, an organic luminescent substance is located in close proximity to the enclosed gas discharge within a plasma-shell, so as to be excited by photons from the enclosed gas discharge and/or gas ionization.

In accordance with one embodiment, an organic photoluminescent substance is positioned on at least a portion of the external surface of a plasma-shell, so as to be excited by photons from the gas discharge within the plasma-shell, such that the excited photoluminescent substance emits visible and/or invisible light.

As used herein organic luminescent substance comprises one or more organic compounds, monomers, dimers, trimers, polymers, copolymers, or like organic materials, which emit visible and/or invisible light when excited by photons from the gas discharge inside of the plasma-shell. Such organic luminescent substances may include one or more organic photoluminescent phosphors selected from organic photoluminescent compounds, organic photoluminescent monomers, dimers, trimers, polymers, copolymers, organic photoluminescent dyes, organic photoluminescent dopants and/or any other organic photoluminescent material. All are collectively referred to herein as organic photoluminescent phosphor.

Organic photoluminescent phosphor substances contemplated herein include those organic light-emitting diodes or devices (OLED) and organic electroluminescent (organic EL) materials, which emit light when excited by photons from the gas discharge of a gas plasma discharge. OLED and organic EL substances include the small molecule organic EL and the large molecule or polymeric OLED.

Small molecule organic EL substances are disclosed in U.S. Pat. No. 4,720,432 (VanSlyke et al.), U.S. Pat. No. 4,769,292 (Tang et al.), U.S. Pat. No. 5,151,629 (VanSlyke), U.S. Pat. No. 5,409,783 (Tang et al.), U.S. Pat. No. 5,645,948 (Shi et al.), U.S. Pat. No. 5,683,823 (Shi et al.), U.S. Pat. No. 5,755,999 (Shi et al.), U.S. Pat. No. 5,908,581 (Chen et al.), U.S. Pat. No. 5,935,720 (Chen et al.), U.S. Pat. No. 6,020,078 (Chen et al.), U.S. Pat. No. 6,069,442 (Hung et al.), U.S. Pat. No. 6,348,359 (VanSlyke et al.), and U.S. Pat. No. 6,720,090 (Young et al.), all incorporated herein by reference. The small molecule organic light-emitting devices may be called SMOLED.

Large molecule or polymeric OLED substances are disclosed in U.S. Pat. No. 5,247,190 (Friend et al.), U.S. Pat. No. 5,399,502 (Friend et al.), U.S. Pat. No. 5,540,999 (Yamamoto et al.), U.S. Pat. No. 5,900,327 (Pei et al.), U.S. Pat. No. 5,804,836 (Heeger et al.), U.S. Pat. No. 5,807,627 (Friend et al.), U.S. Pat. No. 6,361,885 (Chou), and U.S. Pat. No. 6,670,645 (Grushin et al.), all incorporated herein by reference. The polymer light-emitting devices may be called PLED. Organic luminescent substances also include OLEDs doped with phosphorescent compounds as disclosed in U.S. Pat. No. 6,303,238 (Thompson et al.), incorporated herein by reference. Organic photoluminescent substances are also disclosed in U.S. Patent Application Publication No. 2002/0101151 (Choi et al.), 2002/0063525 (Choi et al.), 2003/0003225 (Choi et al.), and 2003/0052596 (Yi et al.), U.S. Pat. No. 6,610,554 (Yi et al.), U.S. Pat. No. 6,692,326 (Choi et al.), International Publications WO 02/104077, and WO 03/046649, incorporated herein by reference.

In one embodiment, the organic luminescent phosphorous substance is a color-conversion-media (CCM) that converts light (photons) emitted by the gas discharge to visible or invisible light. Examples of CCM substances include the fluorescent organic dye compounds.

In another embodiment, the organic luminescent substance is selected from a condensed or fused ring system such as a perylene compound, a perylene based compound, a perylene derivative, a perylene based monomer, dimer or trimer, a perylene based polymer, and/or a substance doped with a perylene.

Photoluminescent perylene phosphor substances are widely known in the prior art. U.S. Pat. No. 4,968,571 (Gruenbaum et al.), incorporated herein by reference, discloses photoconductive perylene materials, which may be used as photoluminescent phosphorous substances. U.S. Pat. No. 5,693,808 (Langhals), incorporated herein by reference, discloses the preparation of luminescent perylene dyes. U.S. Patent Application Publication 2004/0009367 (Hatwar), incorporated herein by reference, discloses the preparation of luminescent materials doped with fluorescent perylene dyes. U.S. Pat. No. 6,528,188 (Suzuki et al.), incorporated herein by reference, discloses the preparation and use of luminescent perylene compounds.

These condensed or fused ring compounds are conjugated with multiple double bonds and include monomers, dimers, trimers, polymers, and copolymers. In addition, conjugated aromatic and aliphatic organic compounds are contemplated including monomers, dimers, trimers, polymers, and copolymers. Conjugation as used herein also includes extended conjugation. A material with conjugation or extended conjugation absorbs light and then transmits the light to the various conjugated bonds. Typically the number of conjugate-double bonds ranges from about 4 to about 15. Further examples of conjugate-bonded or condensed/fused benzene rings are disclosed in U.S. Pat. No. 6,614,175 (Aziz et al.) and U.S. Pat. No. 6,479,172 (Hu et al.), incorporated herein by reference. U.S. Patent Application Publication 2004/0023010 (Bulovic et al.) incorporated herein by reference, discloses luminescent nanocrystals with organic polymers including conjugated organic polymers. Cumulene is conjugated only with carbon and hydrogen atoms. Cumulene becomes more deeply colored as the conjugation is extended. Other condensed or fused ring luminescent compounds may also be used including naphthalimides, substituted naphthalimides, naphthalimide monomers, dimers, trimers, polymers, copolymers and derivatives thereof including naphthalimide diester dyes such as disclosed in U.S. Pat. No. 6,348,890 (Likavec et al.), incorporated herein by reference.

The organic luminescent substance may be an organic luminophore or lumophore, for example as disclosed in U.S. Pat. No. 5,354,825 (Klainer et al.), U.S. Pat. No. 5,480,723 (Klainer et al.), U.S. Pat. No. 5,700,897 (Klainer et al.), U.S. Pat. No. 6,538,263 (Park et al.), and U.S. Pat. No. 7,064,731 (Doyen et al.), all incorporated herein by reference. Also lumophores are disclosed in S E Shaheen et al., *Journal of Applied Physics*, Vol. 84, Number 4, pages 2324 to 2327, Aug. 15, 1998; J. D. Anderson et al., *Journal American Chemical Society*, 1998, Vol. 120, pages 9646 to 9655; and Gyu Hyun Lee et al., *Bulletin of Korean Chemical Society*, 2002, Vol. 23, NO. 3, pages 528 to 530, all incorporated herein by reference.

Application of Organic Phosphors

Organic phosphors may be applied to the plasma-shell with a variety of methods including jetting, spraying, brushing, sheet transfer methods, spin coating, dip coating, or screen-printing. Thin film deposition processes are contemplated including vapor phase deposition and thin film sputtering at temperatures that do not degrade the organic material. This may be done before or after the plasma-shell is added to a substrate or back plate.

Application of Phosphor Before Plasma-Shells are Added to Substrate

If organic phosphors are applied to the plasma-shells before such are applied to the substrate, additional steps may be necessary to place each plasma-shell in the correct position on the substrate.

Inorganic Luminescent Substances

Inorganic luminescent substances or materials such as phosphors may be used alone or in combination with organic luminescent substances. Contemplated combinations include mixtures and/or selective layers of organic and/or inorganic substances. The shell may be made of organic and/or inorganic luminescent substance. In one embodiment the inorganic luminescent substance is incorporated into the particles forming the shell structure.

Two or more luminescent substances may be used in combination with one luminescent substance emitting photons to excite another luminescent substance. In one embodiment, the shell is made of a luminescent substance with the shell exterior containing another luminescent substance. The luminescent shell is excited by photons from a gas discharge within the shell. The exterior luminescent substance produces photons when excited by photons from the excited luminescent shell and/or the gas discharge. The luminescent substance on the exterior of the shell may be organic, inorganic, or a combination of organic and inorganic materials. Typical inorganic luminescent substances are listed below.

Green Phosphor

A green light-emitting phosphor may be used alone or in combination with other light-emitting phosphors such as blue or red. Phosphor materials which emit green light include $Zn_2SiO_4$:Mn, ZnS:Cu, ZnS:Au, ZnS:Al, ZnO:Zn, CdS:Cu, $CdS:Al_2$, $Cd_2O_2S$:Tb, and $Y_2O_2S$:Tb. In one mode and embodiment of this invention, there is used a green light-emitting phosphor selected from the zinc orthosilicate phosphors such as $ZnSiO_4$:$Mn^{2+}$. Green light-emitting zinc orthosilicates including the method of preparation are disclosed in U.S. Pat. No. 5,985,176 (Rao), which is incorporated herein by reference. These phosphors have a broad emission in the green region when excited by 147 nm and 173 nm (nanometers) radiation from the discharge of a xenon gas mixture. In another mode and embodiment of this invention there is used a green light-emitting phosphor which is a terbium activated yttrium gadolinium borate phosphor such as (Gd, Y) $BO_3$:$Tb^{3+}$. Green light-emitting borate phosphors including the method of preparation are disclosed in U.S. Pat. No. 6,004,481 (Rao), which is incorporated herein by reference. In another mode and embodiment there is used a manganese activated alkaline earth aluminate green phosphor as disclosed in U.S. Pat. No. 6,423,248 (Rao), peaking at 516 nm when excited by 147 nm and 173 nm radiation from xenon. The particle size ranges from 0.05 to 5 microns. Rao '248 is incorporated herein by reference. Terbium doped phosphors may emit in the blue region especially in lower concentrations of terbium. For some display applications such as television, it is desirable to have a single peak in the green region at 543 nm. By incorporating a blue absorption dye in a filter, any blue peak can be eliminated. Green light-emitting terbium-activated lanthanum cerium orthophosphate phosphors are disclosed in U.S. Pat. No. 4,423,349 (Nakajima et al.), which is incorporated herein by reference. Green light-emitting lanthanum cerium terbium phosphate phosphors are disclosed in U.S. Pat. No. 5,651,920 (Chau et al.), which is incorporated herein by reference. Green light-emitting phosphors may also be selected from the trivalent rare earth ion-containing aluminate phosphors as disclosed in U.S. Pat. No. 6,290,875 (Oshio et al.).

Blue Phosphor

A blue light-emitting phosphor may be used alone or in combination with other light-emitting phosphors such as green or red. Phosphor materials which emit blue light include ZnS:Ag, ZnS:Cl, and CsI:Na. In a preferred mode and embodiment of this invention, there is used a blue light-emitting aluminate phosphor. An aluminate phosphor which emits blue visible light is divalent europium ($Eu^{2+}$) activated Barium Magnesium Aluminate (BAM) represented by $BaMgAl_{10}O_{17}:Eu^{2+}$. BAM is widely used as a blue phosphor in the PDP industry.

BAM and other aluminate phosphors which emit blue visible light are disclosed in U.S. Pat. No. 5,611,959 (Kijima et al.) and U.S. Pat. No. 5,998,047 (Bechtel et al.), both incorporated herein by reference. The aluminate phosphors may also be selectively coated as disclosed by Bechtel et al. '047. Blue light-emitting phosphors may be selected from a number of divalent europium-activated aluminates such as disclosed in U.S. Pat. No. 6,096,243 (Oshio et al.) incorporated herein by reference. The preparation of BAM phosphors for a PDP is also disclosed in U.S. Pat. No. 6,045,721 (Zachau et al.), incorporated herein by reference.

In another mode and embodiment of this invention, the blue light-emitting phosphor is thulium activated lanthanum phosphate with trace amounts of $Sr^{2+}$ and/or $Li^+$. This exhibits a narrow band emission in the blue region peaking at 453 nm when excited by 147 nm and 173 nm radiation from the discharge of a xenon gas mixture. Blue light-emitting phosphate phosphors including the method of preparation are disclosed in U.S. Pat. No. 5,989,454 (Rao), which is incorporated herein by reference.

In a best mode and embodiment of this invention, a mixture or blend of blue light-emitting phosphors is used such as a blend or complex of about 85% to 70% by weight of a lanthanum phosphate phosphor activated by trivalent thulium ($Tm^{3+}$), $Li^+$, and an optional amount of an alkaline earth element ($AE^{2+}$) as a coactivator and about 15% to 30% by weight of divalent europium-activated BAM phosphor or divalent europium-activated Barium Magnesium, Lanthanum Aluminated (BLAMA) phosphor. Such a mixture is disclosed in U.S. Pat. No. 6,187,225 (Rao), incorporated herein by reference. A blue BAM phosphor with partially substituted $Eu^{2+}$ is disclosed in U.S. Pat. No. 6,833,672 (Aoki et al.) and is also incorporated herein by reference.

Blue light-emitting phosphors also include $ZnO.Ga_2O_3$ doped with Na or Bi. The preparation of these phosphors is disclosed in U.S. Pat. No. 6,217,795 (Yu et al.) and U.S. Pat. No. 6,322,725 (Yu et al.), both incorporated herein by reference. Other blue light-emitting phosphors include europium activated strontium chloroapatite and europium-activated strontium calcium chloroapatite.

Red Phosphor

A red light-emitting phosphor may be used alone or in combination with other light-emitting phosphors such as green or blue. Phosphor materials which emit red light include $Y_2O_2S:Eu$ and $Y_2O_3S:Eu$. In a best mode and embodiment of this invention, there is used a red light-emitting phosphor which is an europium activated yttrium gadolinium borate phosphor such as $(Y,Gd)BO_3:Eu^{3+}$. The composition and preparation of these red light-emitting borate phosphors is disclosed in U.S. Pat. No. 6,042,747 (Rao) and U.S. Pat. No. 6,284,155 (Rao), both incorporated herein by reference. These europium activated yttrium, gadolinium borate phosphors emit an orange line at 593 nm and red emission lines at 611 and 627 nm when excited by 147 nm and 173 nm UV radiation from the discharge of a xenon gas mixture. For television (TV) applications, it is preferred to have only the red emission lines (611 and 627 nm). The orange line (593 nm) may be minimized or eliminated with an external optical filter. A wide range of red light-emitting phosphors are used in the PDP industry and are contemplated in the practice of this invention including europium-activated yttrium oxide.

Other Phosphors

There also may be used phosphors other than red, blue, green such as a white light-emitting phosphor, pink light-emitting phosphor or yellow light-emitting phosphor. These may be used with an optical filter. Phosphor materials which emit white light include calcium compounds such as $3Ca_3(PO_4)_2.CaF:Sb$, $3Ca_3(PO_4)_2.CaF:Mn$, $3Ca_3(PO_4)_2.CaCl:Sb$, and $3Ca_3(PO_4)_2.CaCl:Mn$. White light-emitting phosphors are disclosed in U.S. Pat. No. 6,200,496 (Park et al.) incorporated herein by reference. Pink light-emitting phosphors are disclosed in U.S. Pat. No. 6,200,497 (Park et al.) incorporated herein by reference. Phosphor material which emits yellow light include ZnS:Au.

Organic and Inorganic Luminescent Materials

Inorganic and organic luminescent materials may be used in selected combinations. In one embodiment, multiple layers of luminescent materials are applied to the plasma-shell with at least one layer being organic and at least one layer being inorganic. An inorganic layer may serve as a protective overcoat for an organic layer.

In another embodiment, the plasma-shell comprises or contains inorganic luminescent material. In another embodiment, organic and inorganic luminescent materials are mixed together and applied as a layer inside or outside the plasma-shell. The plasma-shell may also be made of or contain a mixture of organic and inorganic luminescent materials. In one preferred embodiment, a mixture of organic and inorganic material is applied outside the plasma-shell.

Up-Conversion

In one embodiment, there is used an inorganic and/or organic luminescent substance such as a phosphor for up-conversion, for example to convert infrared radiation to visible light. Up-conversion materials including phosphors are disclosed in U.S. Pat. No. 5,541,012 (Ohwaki et al.), U.S. Pat. No. 6,028,977 (Newsome), U.S. Pat. No. 6,265,825 (Asano), and U.S. Pat. No. 6,624,414 (Glesener), all incorporated herein by reference. Up-conversion may also be obtained with shell compositions such as thulium doped silicate glass containing oxides of Si, Al, and La, as disclosed in U.S. Patent Application Publication 2004/0037538 (Schardt et al.), incorporated herein by reference. The glasses of Schardt et al. '538 emit visible or UV light when excited by IR. Glasses for up-conversion are also disclosed in Japanese Patent Publications 9054562 (Akira et al.) and 9086958 (Akira et al.), both incorporated herein by reference.

U.S. Pat. No. 5,166,948 (Gavrilovic), incorporated herein by reference, discloses an up-conversion crystalline structure. U.S. Pat. No. 5,290,730 (McFarlane et al.) discloses a single crystal halide-based up-conversion substance. It is contemplated that the shell may be constructed wholly or in part from an up-conversion material, down-conversion material or a combination of both.

Down-Conversion

The luminescent material may also include down-conversion materials including phosphors as disclosed in U.S. Pat. No. 6,013,538 (Burrows et al.), U.S. Pat. No. 6,091,195 (Forrest et al.), U.S. Pat. No. 6,208,791 (Bischel et al.), U.S. Pat. No. 6,534,916 (Ito et al.), U.S. Pat. No. 6,566,156 (Sturm et al.), U.S. Pat. No. 6,650,045 (Forrest et al.), and U.S. Pat. No. 7,141,920 (Oskam et al.), all incorporated herein by reference. As noted above, the shell may be constructed wholly or in part from a down-conversion material, up-conversion material or a combination of both.

Both up-conversion and down-conversion materials are disclosed in U.S. Pat. No. 3,623,907 (Watts), U.S. Pat. No. 3,634,614 (Geusic), U.S. Pat. No. 3,838,307 (Masi), and U.S. Patent Application Publication No. 2004/0159903 (Burgener, I I et al.), 2004/0196538 (Burgener, I I et al.), and 2005/0094109 (Sun et al.), all incorporated herein by reference. U.S. Pat. No. 6,726,992 (Yadav et al.), incorporated herein by reference, discloses nano-engineered luminescent materials including both up-conversion and down-conversion phosphors.

Application of Luminescent Materials

The organic and/or inorganic luminescent substances are applied by any suitable method to the external surface of the plasma-shell, to the substrate or to any location in close proximity to the gas discharge contained within the plasma-shell. Such methods include thin film deposition methods such as vapor phase deposition, sputtering and E-beam evaporation. Also thick film application methods may be used such as screen-printing, ink jet printing, and/or slurry techniques. Small size molecule OLED materials are typically deposited upon the external surface of the plasma-shell by thin film deposition methods such as vapor phase deposition or sputtering. Large size molecule or polymeric OLED materials are deposited by so called thick film application methods such as screen-printing, ink jet, and/or slurry techniques. If the organic and/or inorganic luminescent substance is applied to the external surface of the plasma-shell, such may be applied as a continuous or discontinuous layer or coating so as to completely or partially cover the plasma-shell with the luminescent substance. A spraying method for depositing phosphors is disclosed in U.S. Pat. No. 5,876,542 (Fujiwara). The luminescent material may also be incorporated into the plasma-shell material and/or added to the inside of the plasma-shell during plasma-shell formation or after the plasma-shell is formed.

Quantum Dots

In one embodiment, the luminescent substance is a quantum dot material. Examples of luminescent quantum dots are disclosed in International Publication No. WO 03/038011, WO 00/029617, WO 03/038011, WO 03/100833, and WO 03/037788, all incorporated herein by reference. Luminescent quantum dots are also disclosed in U.S. Pat. No. 6,468,808 (Nie et al.), U.S. Pat. No. 6,501,091 (Bawendi et al.), U.S. Pat. No. 6,698,313 (Park et al.), and U.S. Patent Application Publication 2003/0042850 (Bertram et al.), all incorporated herein by reference. The quantum dots may be added or incorporated into the plasma-shell during plasma-shell formation or after the plasma-shell is formed.

Protective Overcoat for Luminescent Substance

In one embodiment, an organic and/or inorganic luminescent substance is located on an external surface of the plasma-shell and/or at an external location such as on the substrate near the plasma-shell. Organic luminescent phosphors are particularly suitable for placing on the exterior plasma-shell surface, but may require a protective overcoat. The protective overcoat may be inorganic, organic, or a combination of inorganic and organic. This protective overcoat may be an inorganic and/or organic luminescent material.

The luminescent substance may have a protective overcoat such as a clear or transparent acrylic compound including acrylic solvents, monomers, dimers, trimers, polymers, copolymers, and derivatives thereof to protect the luminescent substance from direct or indirect contact or exposure with environmental conditions such as air, moisture, sunlight, handling, or abuse. The selected acrylic compound is of a viscosity such that it can be conveniently applied by spraying, screen print, ink jet, or other convenient methods so as to form a clear film or coating of the acrylic compound over the luminescent substance.

Other organic compounds may also be suitable as protective overcoats including silanes such as glass resins. Also the polyesters such as Mylar® may be applied as a spray or a sheet fused under vacuum to make it wrinkle free. Polycarbonates may be used but may be subject to UV absorption and detachment.

In one embodiment hereof the luminescent substance is coated with a film or layer of a parylene compound including monomers, dimers, trimers, polymers, copolymers, and derivatives thereof. The parylene compounds are widely used as protective films. Specific compounds including poly-monochloro-para-xylyene (Parylene C) and poly-para-xylylene (Parylene N). Parylene polymer films are also disclosed in U.S. Pat. No. 5,879,808 (Wary et al.) and U.S. Pat. No. 6,586,048 (Welch et al.), both incorporated herein by reference. The parylene compounds may be applied by ink jet printing, screen printing, spraying, and so forth as disclosed in U.S. Patent Application Publication 2004/0032466 (Deguchi et al.), incorporated herein by reference. Parylene conformal coatings are covered by Mil-I-46058C and ISO 9002. Parylene films may also be induced into fluorescence by an active plasma as disclosed in U.S. Pat. No. 5,139,813 (Yira et al.), incorporated herein by reference.

Phosphor overcoats are also disclosed in U.S. Pat. No. 4,048,533 (Hinson et al.), U.S. Pat. No. 4,315,192 (Skwirut et al.), U.S. Pat. No. 5,592,052 (Maya et al.), U.S. Pat. No.

5,604,396 (Watanabe et al.), U.S. Pat. No. 5,793,158 (Wedding), and U.S. Pat. No. 6,099,753 (Yoshimura et al.), all incorporated herein by reference. In some embodiments, the luminescent substance is selected from materials that do not degrade when exposed to oxygen, moisture, sunlight, etc. and that may not require a protective overcoat. Such include various organic luminescent substances such as the luminescent perylene compounds disclosed above. For example, luminescent perylene compounds may be used and do not require a protective overcoat.

Plasma-Shells Combined with Plasma-Tubes

The structure may comprise a combination of gas-filled plasma-shells and gas-filled elongated plasma-tubes. Gas-filled elongated tubes are disclosed in U.S. Pat. No. 3,602,754 (Pfaender et al.), U.S. Pat. No. 3,654,680 (Bode et al.), U.S. Pat. No. 3,927,342 (Bode et al.), U.S. Pat. No. 4,038,577 (Bode et al.), U.S. Pat. No. 3,969,718 (Strom), U.S. Pat. No. 3,990,068 (Mayer et al.), U.S. Pat. No. 4,027,188 (Bergman), U.S. Pat. No. 5,984,747 (Bhagavatula et al.), U.S. Pat. No. 6,255,777 (Kim et al.), U.S. Pat. No. 6,633,117 (Shinoda et al.), U.S. Pat. No. 6,650,055 (Ishimoto et al.), and U.S. Pat. No. 6,677,704 (Ishimoto et al.), all incorporated herein by reference.

As used herein, the elongated gas-filled plasma-tube is intended to include capillary, filament, filamentary, illuminator, hollow rod, or other such terms. It includes an elongated enclosed gas-filled structure having a length dimension that is greater than its width dimension. The width of the gas-filled plasma-tube is the viewing width from the top or bottom. A gas-filled plasma-tube has multiple gas discharge cells or pixels of 100 or more, typically 500 to 1000 or more, whereas a gas-filled plasma-shell typically has only one gas discharge cell. In some embodiments, the gas-filled plasma-shell may define more than one cell, i.e., 2, 3, or 4 cells up to 10 cells.

The length of each gas-filled plasma-tube may vary depending upon the length of the structure. In one embodiment hereof, an elongated tube is selectively divided into a multiplicity of lengths. In another embodiment, there is used a continuous tube that winds or weaves back and forth from one end to the other end of the detector.

The gas-filled plasma-shells and/or gas-filled plasma-tubes may be arranged in any configuration. In one embodiment, there are alternating rows of gas-filled plasma-shells and gas-filled plasma-tubes. The gas-filled plasma-tubes may be used for any desired function or purpose including the priming or conditioning of the gas-filled plasma-shells. In one embodiment, the tubes are arranged around the perimeter of the detector to provide priming or conditioning of the gas in the plasma-shells. The tubes may be of any geometric cross-section including circular, elliptical, square, rectangular, triangular, polygonal, trapezoidal, pentagonal, or hexagonal. The tube may contain secondary electron emission materials, luminescent materials, and reflective materials as discussed herein for shells. The gas-filled plasma-tubes and/or the shells may be positioned and spaced in a structure so as to utilize positive column discharge. Elongated tubes with positive column discharge is disclosed in U.S. Pat. Nos. 7,176,628, 7,157,854 and 7,122,961 all issued to Carol Ann Wedding and incorporated herein by reference.

Combinations of Plasma-Shells

The UV germicidal system may comprise shells with different geometric shapes, shells made of different materials, and shells filled with different gases.

Combinations of plasma-shells with two or more different geometric shapes include plasma-spheres and plasma-discs, plasma-spheres and plasma-domes, plasma-discs and plasma-domes, plasma-cube, and plasma-cuboid, and three or more such as plasma-spheres, plasma-discs, plasma-domes and plasma-disc, plasma-cubes, and plasma-domes. The plasma-shell material may vary from plasma-shell to plasma-shell including from geometric shape to geometric shape. plasma-shells of the same or different geometric shape may be filled with different gases.

The geometric shape of the shells, plasma-shell material, and gas may vary from plasma-shell to plasma-shell within a given device. Thus one plasma-shell in a device of a selected geometric shape may be made of one material and contain one gas while another plasma-shell of the same or different geometric shape may be made of the same or a different material and/or contain the same or a different gas.

Shells may also be positioned or located closely together for more effective radiation. The shells may be stacked in two or more layers. The shells may also be located on opposite sides of the same substrate.

Selected hollow shells may be filled with one gas and other selected hollow shells may be filled with a different gas.

Selected hollow shells may be made of one luminescent material and other selected hollow shells may be made of a different luminescent material.

Conduit Material

The water conduit may comprise a pipe, tube or other means. It may be made of any UV stable material such as, copper, ethylene propylene diene Monomer (EPDM), or a combination of such materials.

Other Applications

In accordance with another embodiment of this invention, a multiplicity of gas-filled shells are used to emit light in the UV region to erase stored information held in Erasable Programmable Read-Only Memory or EPROMs. Other applications envisioned include treatment of skin for cosmetic or medical reasons, and curing of materials including but not limited to polymers and adhesives, UV vapor deposition, and a device to emit UV light as a catalyst for chemical reactions.

SUMMARY

The foregoing description of various preferred embodiments of the invention has been presented for purposes of illustration and description. It is not intended to be exhaustive or to limit the invention to the precise forms disclosed. Obvious modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims to be interpreted in accordance with the breadth to which they are fairly, legally, and equitably entitled.

The invention claimed is:

1. An ultraviolet (UV) light-emitting device with a UV light-emitting source to induce a chemical reaction, the UV light-emitting source comprising a multiplicity of hollow shells filled with a gas that emits radiation during gas discharge, said shells being located on opposing sides of a substrate and encapsulating the gas independently of the substrate, said shells being made of a luminescent material that emits UV light when activated by radiation from the gas discharge, the gas discharge inside each hollow shell being excited by a gas discharge voltage from conductors located on the substrate, said substrate and shells being in direct contact with a selected substance to UV induce the chemical reaction.

2. The device of claim 1 in which an array of hollow shells are assembled with different hollow shells in the array emitting UV light in different spectral regions, including UVA, UVB, or UVC.

3. The device of claim 1 in which one or more hollow shells are partially or wholly coated with a titanium oxide.

4. The device of claim 3 in which the titanium oxide is doped with tungsten trioxide.

5. The device of claim 1 wherein selected hollow shells are filled with one gas and other selected hollow shells are filled with a different gas.

6. The device of claim 1 wherein selected hollow shells are made of one luminescent material and other selected hollow shells are made of a different luminescent material.

7. The device of claim 1 wherein the hollow shells are stacked in two or more layers.

8. The device of claim 1 wherein selected hollow shells are of one geometric shape and other selected shells are of a different geometric shape.

9. The device of claim 1 wherein the hollow shells are packed closely together in an array to provide a lambertian light source devoid of hot spots and shadows.

10. An ultraviolet (UV) curing device comprising a substrate with two opposing sides, a multiplicity of gas filled shells located on each opposing side, each shell connected to one or more conductors that provide a gas discharge voltage to each shell to produce UV light emission from each shell, said substrate and shells being in direct contact with a selected substance for UV curing of the substance.

11. The device of claim 10 in which an array of shells are assembled on one or both sides of the substrate with different shells in the array emitting UV light in different spectral regions, including UVA, UVB, or UVC.

12. The device of claim 10 in which one or more shells are partially or wholly coated with a selected material to enhance the UV curing of the substance.

13. The device of claim 12 in which the selected material is a titanium oxide.

14. The device of claim 13 in which the titanium oxide is doped with tungsten trioxide.

15. The device of claim 10 wherein the shells are partially or wholly constructed of a luminescent material that emits UV when excited by radiation from the gas discharge in said shells.

16. The device of claim 15 wherein each shell is partially or wholly coated with titanium oxide.

17. The device of claim 16 wherein the titanium oxide is doped with tungsten trioxide.

18. The device of claim 10 wherein the shells are packed closely together in an array to provide a lambertian light source devoid of hot spots and shadows.

* * * * *